United States Patent
Amini

(10) Patent No.: US 6,744,263 B2
(45) Date of Patent: Jun. 1, 2004

(54) APPARATUS AND METHOD FOR THE MEASUREMENT OF ELECTRICAL PROPERTIES OF MATERIALS THROUGH NON-MAGNETIZABLE MATERIALS

(75) Inventor: Bijan K. Amini, Houston, TX (US)

(73) Assignee: EM-Tech Sensors LLC, Houston, TX (US)

( * ) Notice: Subject to any disclaimer, the term of this patent is extended or adjusted under 35 U.S.C. 154(b) by 65 days.

(21) Appl. No.: 09/734,528

(22) Filed: Dec. 11, 2000

(65) Prior Publication Data

US 2002/0097057 A1 Jul. 25, 2002

Related U.S. Application Data

(60) Provisional application No. 60/170,172, filed on Dec. 10, 1999.

(51) Int. Cl.[7] .......................... G01R 27/04; G01N 27/72
(52) U.S. Cl. ...................... 324/644; 324/632; 324/232; 324/239
(58) Field of Search ................... 324/644, 632, 324/232, 228, 241, 334, 335, 340, 339, 239

(56) References Cited

U.S. PATENT DOCUMENTS

| | | | |
|---|---|---|---|
| 3,574,458 A | | 4/1971 | Hollis |
| 3,617,779 A | | 11/1971 | Rosenberg |
| 3,644,823 A | * | 2/1972 | Dowling et al. ............ 324/340 |
| 3,851,236 A | | 11/1974 | Dennhardt |
| 3,882,375 A | * | 5/1975 | Zemanek, Jr. ............. 324/340 |
| 3,995,835 A | | 12/1976 | Clichy |
| 4,679,936 A | | 7/1987 | Gerharz |
| 5,038,107 A | | 8/1991 | Gianzero |
| 5,132,623 A | | 7/1992 | De |
| 5,150,446 A | | 9/1992 | Penner |
| 5,260,661 A | | 11/1993 | Vail |
| 5,283,520 A | | 2/1994 | Martin |
| 5,426,367 A | | 6/1995 | Martin |
| 5,610,517 A | | 3/1997 | Ma |
| 5,633,182 A | | 5/1997 | Miyawaki |
| 5,646,533 A | * | 7/1997 | Locatelli et al. ............ 324/339 |
| 5,654,639 A | * | 8/1997 | Locatelli et al. ............ 324/239 |
| 5,698,977 A | | 12/1997 | Simpson |
| 5,751,144 A | | 5/1998 | Weischedel |
| 5,942,894 A | | 8/1999 | Wincheski |
| 5,969,254 A | | 10/1999 | Yamaguchi |
| 6,008,657 A | | 12/1999 | Suyama |
| 6,025,721 A | | 2/2000 | Vail |
| 6,084,403 A | | 7/2000 | Sinclair |
| 6,097,532 A | | 8/2000 | Harris |
| 6,100,696 A | | 8/2000 | Sinclair |
| 6,157,195 A | | 12/2000 | Vail |

* cited by examiner

*Primary Examiner*—Christine Oda
*Assistant Examiner*—Anjan K. Deb
(74) *Attorney, Agent, or Firm*—David McEwing

(57) ABSTRACT

A method and apparatus is disclosed for measuring electrical properties of objects by the transmission of electromagnetic waves through a non-magnetizable material. The disclosure also describes a method of measuring changes in electromagnetic signals as the amplitude and frequency of the electromagnetic waves is varied to determine the thickness of an object.

2 Claims, 34 Drawing Sheets

APPARATUS AND METHOD FOR THE MEASUREMENT OF ELECTRICAL PROPERTIES OF MATERIALS THROUGH NON-MAGNETIZABLE MATERIALS

CROSS REFERENCE TO RELATED APPLICATION

The present application is a continuation-in-part application of the application of Bijan Amini, U.S. Ser. No. 60/170,172, filed Dec. 10, 1999, entitled "Apparatus And Method For The Measurement Of Electrical Properties Of Materials Through Non-Magnetizable Materials."

FIELD OF THE INVENTION

The present invention relates generally to utilizing controlled transmissions of electromagnetic (EM) energy through or across non-magnetizable materials that have previously been barriers to penetration to determine the thickness and EM characteristics of materials.

BACKGROUND OF THE INVENTION

It has long been possible to measure metallic thickness variations by electromagnetics. Prior methods have typically excited the metal by eddy currents or D.C. fields. After excitation, the known methods looked for variations in amplitude of the signal corresponding to variations in metallic thickness.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features, and advantages and in accordance with the purpose of the invention as embodied and broadly described herein, a method for the measurement of electrical properties of materials through non-magnetizable materials is provided. The method is also used to calculate the thickness of a material with unknown permeability and conductivity using transparencies. The method comprising the steps of creating a first set of electromagnetic waves having specific constant amplitude of a known frequency, the first set of electromagnetic waves for engaging a system, impinging the first set of electromagnetic waves on the system under investigation, nulling the system, receiving a nulled signal, creating a change in the system, and receiving a modified signal associated with the change from the nulled signal such that the modified signal contains sufficient information to determine the change in the system.

The method further comprising the steps of testing empirically to approximate the conductivity, testing empirically to approximate the permeability, creating a second set of electromagnetic waves adjacent to the system to be measured, the second set of electromagnetic waves being of a relatively low frequency and of lower frequency that the first set of electromagnetic waves, and impinging the second set of electromagnetic waves on the system for saturating a portion of the material in the system.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

FIGS. 1A 1B, 1C and 1D illustrate various configurations for geometric nulling as practiced by the present invention. Particularly, FIGS. 1A 1B, 1C and 1D illustrate geometric nulling as practiced by the present invention with respect to spacial equivalence, equivalence of windings, current equivalence and magnetic moment equivalence, respectively. In practicing the present invention, several magnetic relationships or phenomena are of assistance. The magnetomotive force F can be expressed in ampere-turns, NI, where N is the number of turns linked with the magnetic circuit and I is the current. The magnetic field intensity H is equal to the amperes per meter I/L, which can be expressed as the flux density divided by the permeability $\beta/\mu$. The flux $\Phi$ can be expressed as:

$$\Phi = BA = k_1 NI(L/A\mu)$$

where k1 is a constant,

NI is the ampere-turns,

L is the length of the magnetic path,

A is the area, and $\mu$ is the permeability.

Therefore, $$NI = k_2 BL$$

where $k_2$ is a constant,

B is the flux density, and

L is the length of the magnetic path.

The direction of the magnetizing force of a current is at right angles to its direction of flow of the current. For a cylinderical conductor carrying a current, the magnetic lines about the cylinderical conductor are in circular planes concentric with the conductor and normal to the conductor. The curved lines used to represent a magnetic field are drawn such that the number of lines is related to the strength of the magnetic field at a given point and the tangent of any curve at a particular point is along the direction of magnetic force at that point.

The direction of the current I and the resulting magnetic field H are related to each other by the so-called "corkscrew rule." The corkscrew rule compares the forward travel of the corkscrew with the current I, and the direction in which the corkscrew is rotated with the resulting magnetic field H. Another tool for visualizing the effects associated with the present invention is to use the "right hand rule." The right hand rule requires that the conductor is grasped in the right hand with the thumb pointing in the direction the current is flowing. With the conductor in the right hand, the fingers will point in the direction of the lines of flux.

Figure 1A:
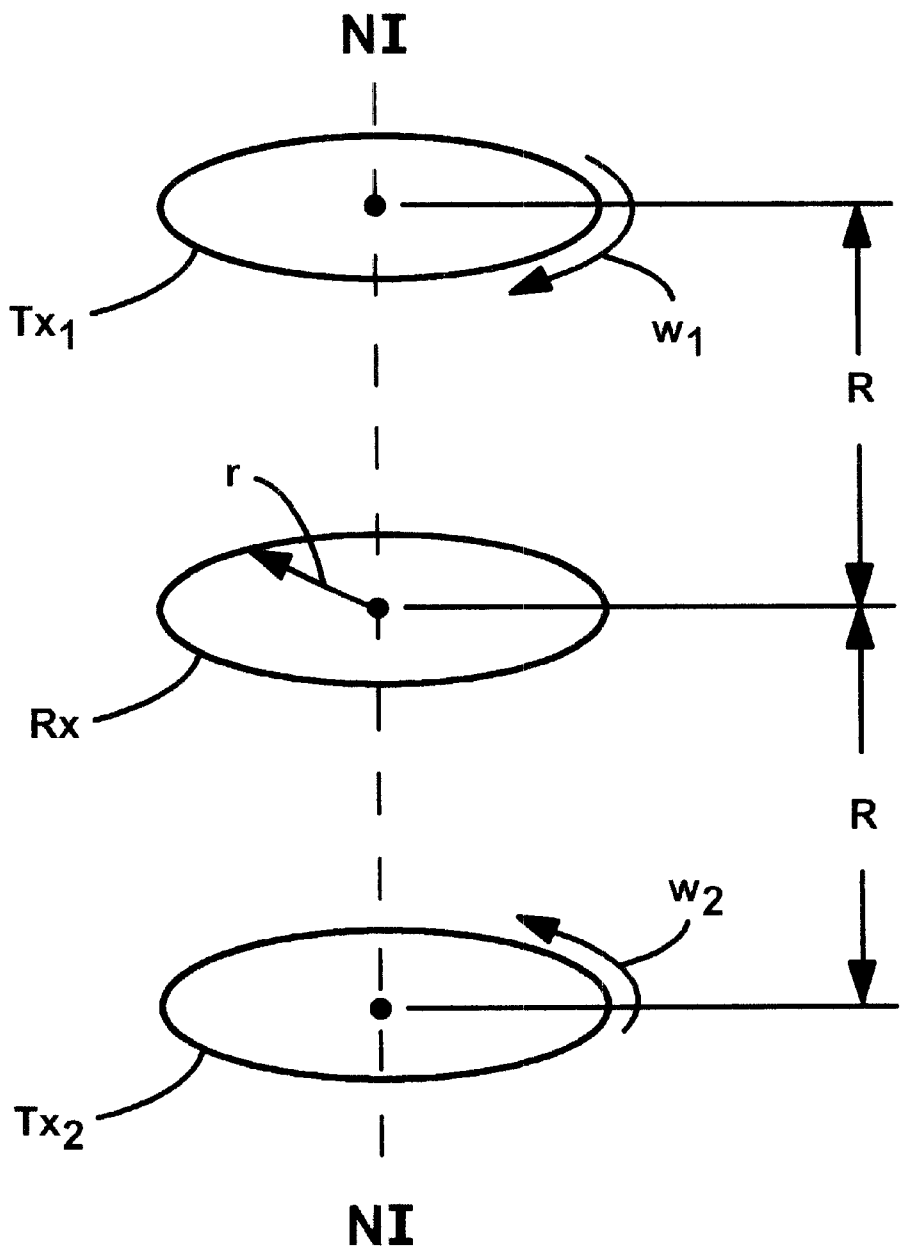
FIGS. 1A, 1B, 1C and 1D illustrate geometric nulling as practiced by the present invention with respect to spacial equivalence, equivalence of windings, current equivalence and magnetic moment equivalence, respectively.

FIG. 1A illustrates geometric nulling using spacial equivalence. Nulling using spacial equivalence provides that the receiver Rx and the transmitters $Tx_1$, $Tx_2$ are equidistant. Thus, the receiver Rx is disposed intermediate between, and equal distance from, the first transmitter $Tx_1$ and the second transmitter $Tx_2$. The distance R between the transmitters $Tx_1$, $Tx_2$ and the receiver Rx is equal. The coils associated with the transmitters $Tx_1$, $Tx_2$ are wound in different or opposite directions. Winding the transmitters $Tx_1$, $Tx_2$ in opposite directions provides a "bucking" relationship for the transmitters $Tx_1$, $Tx_2$. The coil associated with the first transmitter $Tx_1$ is wound in a clockwise direction $w_1$. The coil associated with the second transmitter $Tx_2$ is wound in a counter clockwise direction $w_2$. The coil associated with the receiver Rx can be wound in either direction. When the transmitters $Tx_1$, $Tx_2$ are bucked, i.e., wound in opposite directions, the field lines generated are typically described using the right thumb rule. Thus, bucking provides a canceling of the respective field lines associated with the bucked transmitters. A quantity of current I is applied to the transmitters $Tx_1$, $Tx_2$. The receiver Rx is illustrated having a specified radius r. In one embodiment, the transmitters $Tx_1$, $Tx_2$ have a coil with a specified number of turns N. It is appreciated by those skilled in the art that the number of turns $N_T$ for any transmitter $Tx_1$, $Tx_2$ does not have to be equal to the number of turns NR for the receiver Rx.

Figure 1B:
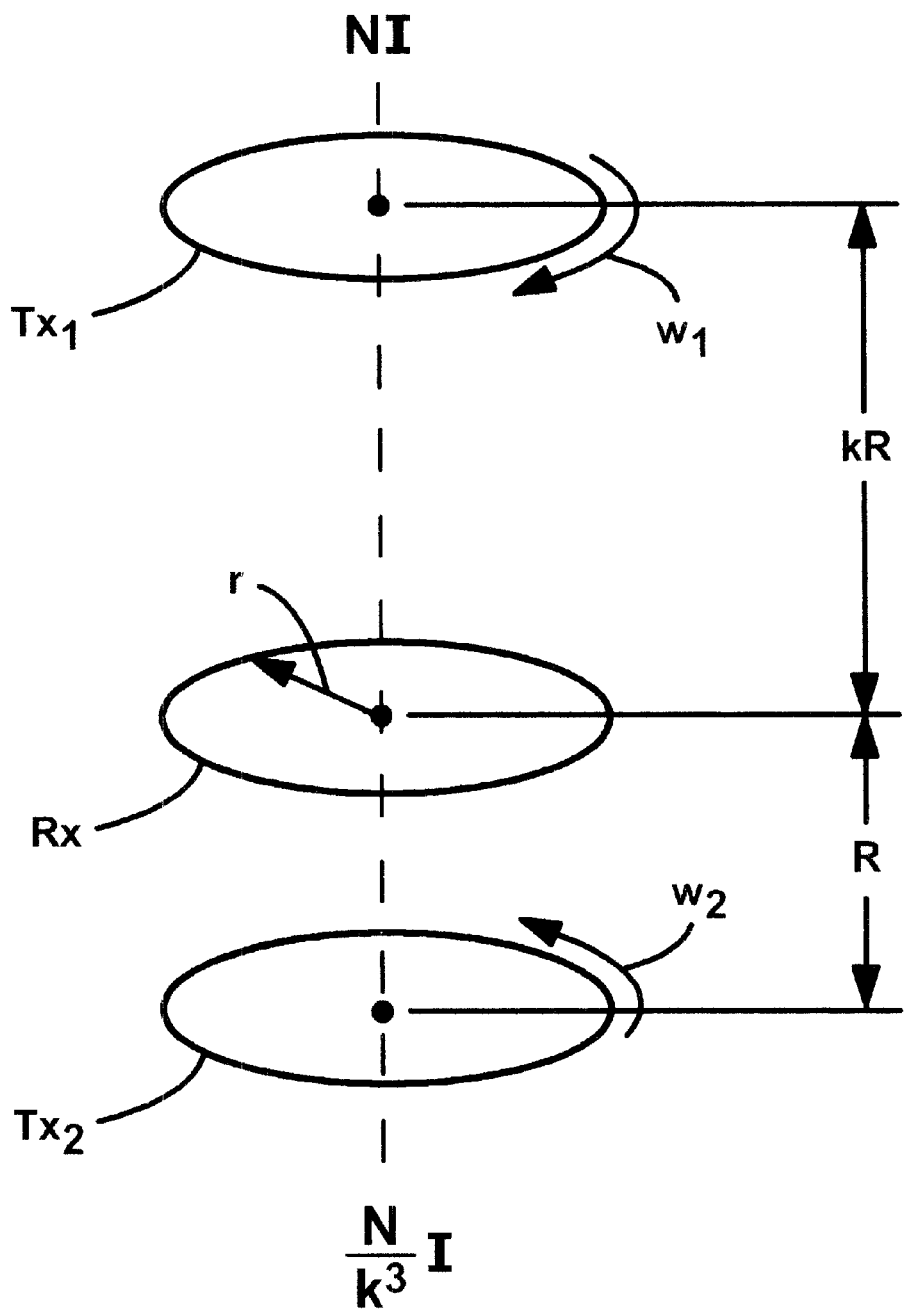

FIG. 1B illustrates geometric nulling using equivalence of windings as practiced by the present invention. Nulling using winding equivalence, or the number of turns N, provides equivalence with respect to the number of turns N associated with the coils of the relevant transducer; be it transmitter Tx or receiver Rx. The coils associated with the transmitters $Tx_1$, $Tx_2$ are wound in different or opposite directions. Winding the transmitters $Tx_1$, $Tx_2$ in opposite directions provides a "bucking" relationship for the transmitters $Tx_1$, $Tx_2$. The coil associated with the first transmitter $Tx_1$ is wound in a clockwise direction $w_1$. The coil associated with the second transmitter $Tx_2$ is wound in a counter clockwise direction $w_2$. The coil associated with the receiver Rx can be wound in either direction. When the transmitters $Tx_1$, $Tx_2$ are bucked, i.e., wound in opposite directions, the field lines generated are typically described using the right thumb rule. Thus, bucking provides a canceling of the respective field lines associated with the bucked transmitters. A quantity of current I is applied to the transmitters $Tx_1$, $Tx_2$. The receiver Rx is illustrated having a specified radius r.

FIG. 1B illustrates a receiver Rx disposed between a first transmitter $Tx_1$ and a second transmitter $Tx_2$. The distance the receiver Rx is between two transmitters $Tx_1$, $Tx_2$ differs. Particularly, distance between the receiver Rx and the transmitter $Tx_2$ is the distance R. The distance between the receiver Rx and the first transmitter $Tx_1$ is the distance kR. The radius r of the coils associated with the receiver Rx is noted on the drawing having a specified radius r. It is know to those skilled in the art that the flux field decreases or drops off as a function of one over $R^3$, where R is the distance between the two transmitters. More particularly, given R is greater than or equal to r, then the power varies as the cube of the coefficient k of the distance R. Thus, to achieve geometric nulling, and thus equivalence with respect to the number of turns N, the relationship between the number of turns N for the first transmitter $Tx_1$ and the number of turns associated with the second transmitter $Tx_2$ is the number of turns divided by the cube of the coefficient k $N/k^3$. Therefore, when the first transmitter $Tx_1$ has the number of turns N and is a distance kR from the receiver Rx, then the second transmitter $Tx_2$, being a distance R from the receiver Rx, requires that the number of turns N be divided by $k^3$ where the distance between the receiver Rx and the transmitter $Tx_1$ is kR.

Figure 1C:
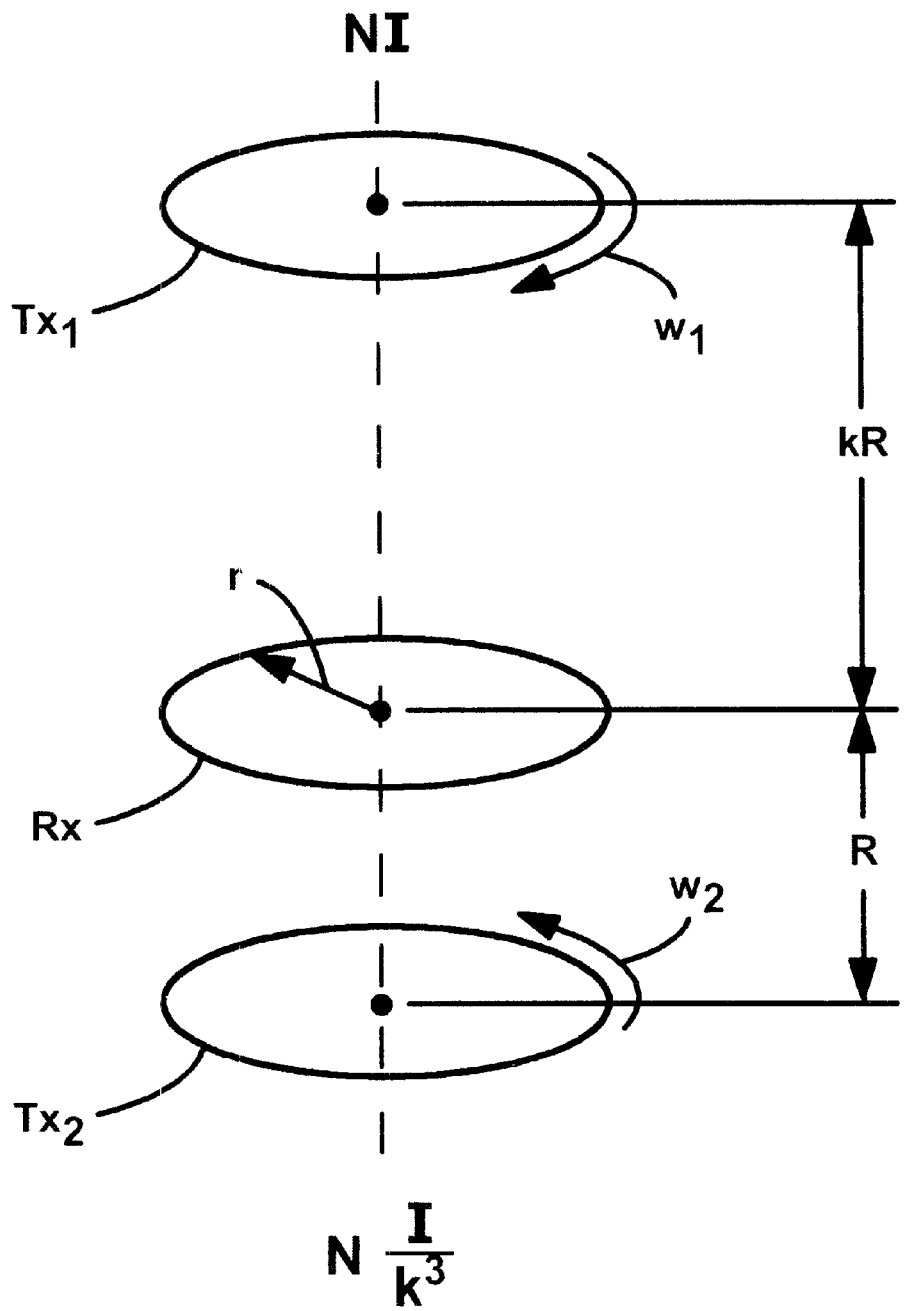

FIG. 1C is illustrates a configuration used with the present invention for geometrically nulling with respect to current equivalence. Particularly, a receiver Rx is disposed between a first transmitter $Tx_1$ and a second transmitter $Tx_2$ such that the receiver is a distance R from the second transmitter $Tx_2$. Also, the first transmitter $Tx_1$ is a distance kR from the receiver Rx where k is a constant and r is a constant. To maintain current equivalence with respect to geometric nulling, the value of the current I on the first transmitter $Tx_1$ has the relationship of the current varying as the cube of the distance $R^3$. Thus, the second transmitter $Tx_2$ requires a current of I divided by $k^3$ or $I/k^3$. As with geometric nulling for the number of turns N, geometric nulling for current equivalence in the illustrated configuration requires that R is greater than or equal to the radius of the coil r where r is the radius of the coil windings for the receiver Rx. The coils associated with the transmitters $Tx_1$, $Tx_2$ are wound in different or opposite directions. Winding the transmitters $Tx_1$, $Tx_2$ in opposite directions provides a "bucking" relationship for the transmitters $Tx_1$, $Tx_2$. The coil associated with the first transmitter $Tx_1$ is wound in a clockwise direction $w_1$. The coil associated with the second transmitter $Tx_2$ is wound in a counter clockwise direction $W_2$. The coil associated with the receiver Rx can be wound in either direction. When the transmitters $Tx_1$, $Tx_2$ are bucked, i.e., wound in opposite directions, the field lines generated are typically described using the right thumb rule. Thus, bucking provides a canceling of the respective field lines associated with the bucked transmitters. A quantity of current I is applied to the transmitters $Tx_1$, $Tx_2$. The receiver Rx is illustrated having a specified radius r.

Figure 1D:
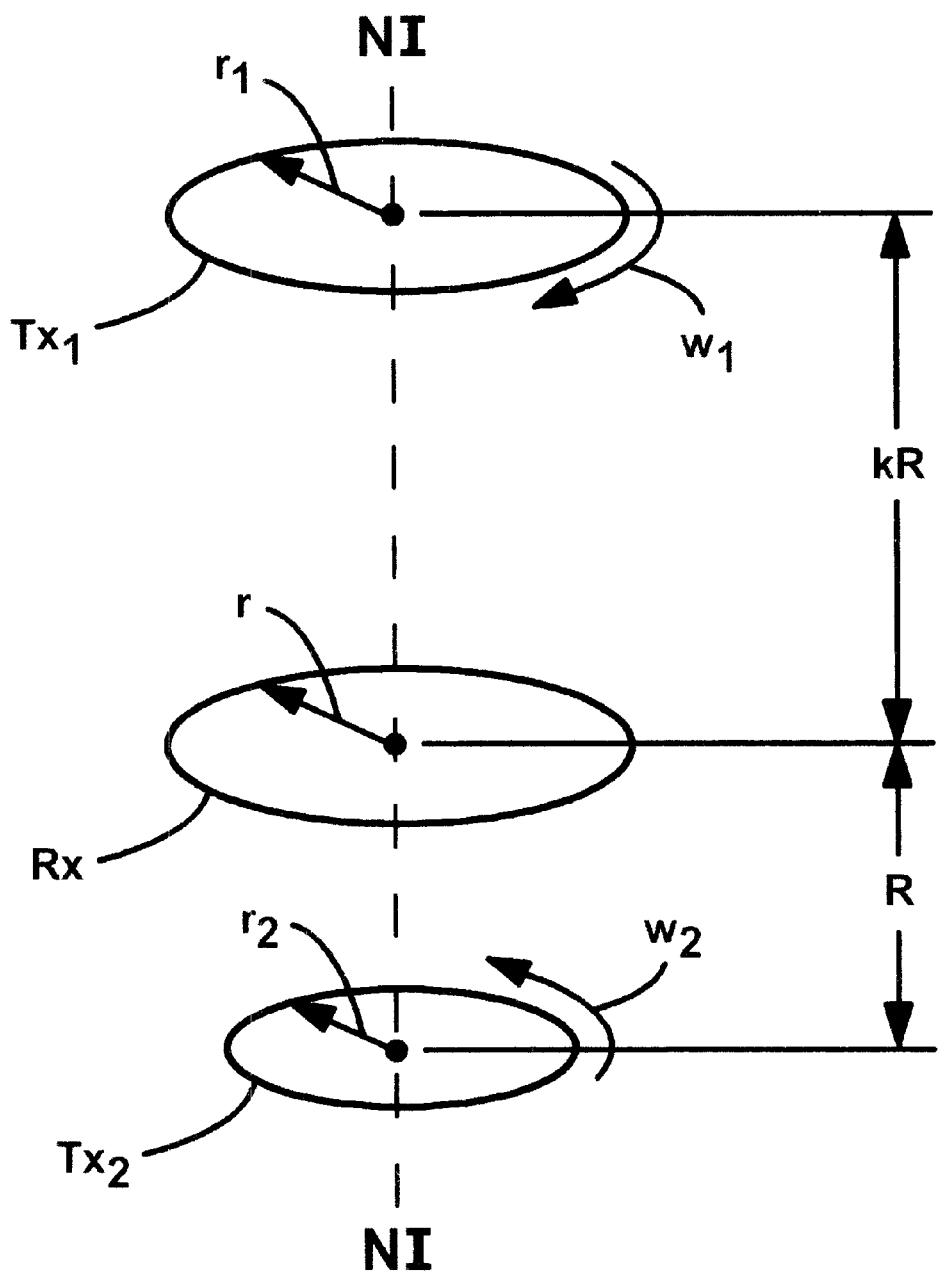

FIG. 1D illustrates a configuration for the present invention which achieves geometric nulling with magnetic moment equivalence. To achieve magnetic moment equivalence, a receiver Rx is disposed between a first transmitter $Tx_1$ and a second transmitter $Tx_2$ such that the receiver Rx and the second transmitter $Tx_2$ are disposed at a distance R apart. The receiver Rx and the first transmitter $Tx_1$ are disposed at another distance kR apart, where k is a constant and R is the distance between the receiver Rx and the second transmitter $Tx_2$. Magnetic moment equivalence provides for using transmitters having differing coil radius r. The radius $r_1$ for the coil of the first transmitter $Tx_1$ is proportionately larger than the radius $r_2$ for the coil for the second transmitter $Tx_2$. Thus, the coil for the first transmitter $Tx_1$ is proportionately larger than the coil for the second transmitter $Tx_2$, and the first transmitter $Tx_1$ is disposed by a factor k further away from the receiver Rx than the second transmitter $Tx_2$. The coils associated with the transmitters $Tx_1$, $Tx_2$ are wound in different or opposite directions. Winding the transmitters $Tx_1$, $Tx_2$ in opposite directions provides a "bucking" relationship for the transmitters $Tx_1$, $Tx_2$. The coil associated with the first transmitter $Tx_1$ is wound in a clockwise direction $w_1$. The coil associated with the second transmitter $Tx_2$ is wound in a counter clockwise direction $W_2$. The coil associated with the receiver Rx can be wound in either direction. When the transmitters $Tx_1$, $Tx_2$ are bucked, i.e., wound in opposite directions, the field lines generated are typically described using the right thumb rule. Thus, bucking provides a canceling of the respective field lines associated with the bucked transmitters. A quantity of current I is applied to the transmitters $Tx_1$, $Tx_2$. The receiver Rx is illustrated having a specified radius r, and the transmitters $Tx_1$, $Tx_2$ are illustrated having differing radius $r_1$, $r_2$.

FIGS. 1A, 1B, 1C and 1D all illustrate varying configurations used with the present invention for geometric nulling. It should be appreciated that all of the transmitters Tx and the receivers Rx can be reversed geometrically. Thus, where a receiver Rx is disposed between two transmitters $Tx_1$, $Tx_2$, geometric reversal would provide for a single transmitter Tx being disposed between a first receiver $Rx_1$ and second receiver $Rx_2$. Further, there are different items that can be varied to achieve geometric nulling in practicing the present invention. As discussed, the number of turns N can be changed, current equivalence can be maintained, spacial equivalence can be maintained and magnetic moment equivalence can be maintained. Also, the wire size can be varied with respect to the gauge or diameter. The core material can be changed, the thickness of the insulation can be changed and the type of insulation can be changed.

Figure 2:
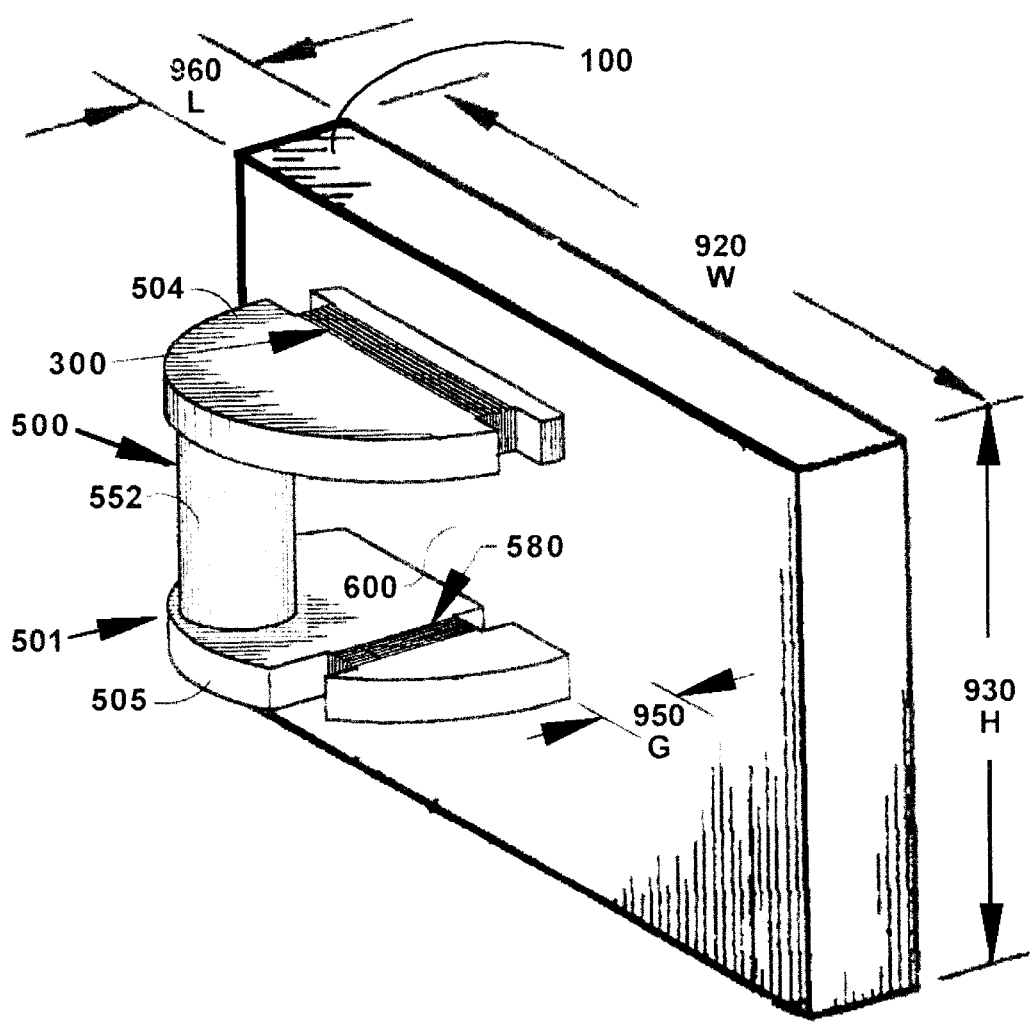
FIG. 2 illustrates the flux circuit core of one embodiment of the magnetic transparency generator used to generate the transparency current required in practicing the present invention.

FIG. 2 illustrates one embodiment of a magnetic transparency generator 500 used to generate the transparency current required in practicing the present invention. The magnetic transparency generator 500 provides for containing flux lines capable of completely saturating the intended barrier material 100 volume region. Also, FIG. 2 illustrates one embodiment of the flux circuit core 501 for use with the present invention. The flux circuit core 501 comprises a top flange 504, a bottom flange 505 and a core 552. The core 552 is located between the top flange 504 and bottom flange 505. The tank wall comprises the barrier material 100. The magnetic transparency generator 500 incorporates the flux circuit core 501 for providing a transparent volume region that is illustrated having a width W 920, a height H 930 and a thickness L 960. The barrier volume region may be termed the target material. It is appreciated that the transmitter coils 300 and the receiver coils 580 are in positions of geometric nulling with respect to the magnetic transparency generator 500 illustrated.

Figure 3:
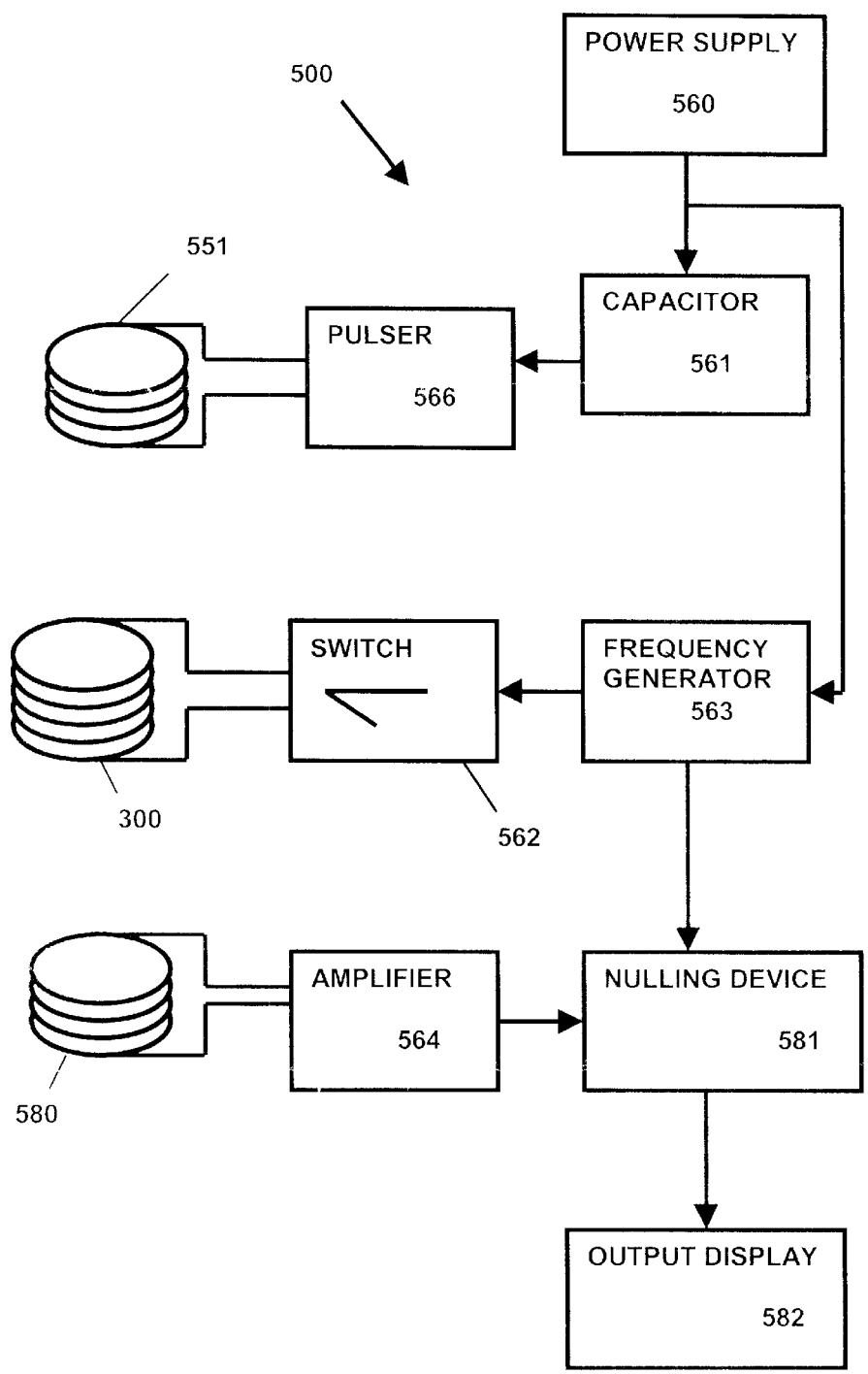
FIG. 3 is a block diagram of one embodiment of a magnetic transparency generator of the present invention.

FIG. 3 is a block diagram of one embodiment of a magnetic transparency generator 500 of the present invention. The magnetic transparency generator 500 comprises a large coil 551, a small coil 300, and a receiver coil 580. The large coil 551 generates the transparency current. The small coil 300 generates the transmitter signal. The receiver coil 580 accepts the returning transmitter signal. The large coil 551 for generating the transparency current is engaged with a pulser 566, one or more capacitors 561 and a power source 560. The small coil 300 of the transmitter and the receiver coil 580 are engaged with a switch 562, a frequency generator 563, a low noise amplifier (LNA) 564, an electrical nulling circuit 581 for digital signal processing and an output means 582. For the present invention, the components associated with the large coil 551 for generating the transparency current are not used, but are illustrated for completeness.

Figure 4:
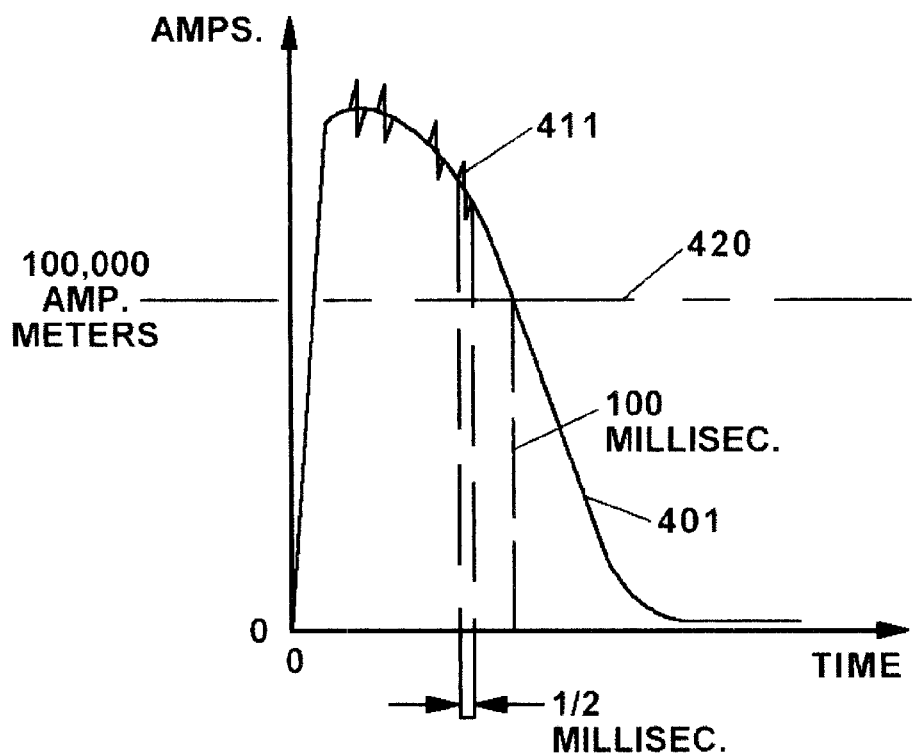
FIG. 4 illustrates a graph of current versus time with respect to the present invention.

FIG. 4 illustrates a graph of current versus time with respect to the present invention. FIG. 4 illustrates three significant features in practicing the present invention: the current level required for saturation 420, the higher frequency sensing signal 411 and the lower frequency transparency signal 401. The higher frequency sensing signal 411 may be imposed on the lower frequency transparency signal 401. FIG. 4 illustrates as spikes 411 the higher frequency oscillating electromagnetic wave of the sensing signal 411 disposed along a lower frequency oscillating transparency current 401. In one embodiment of the present invention, the sensing signal 411 may be transmitted only during the duration of each cycle of the oscillating transparency current 401 that is above the level 420 required for saturation. Among other advantages, the latter embodiment minimizes energy consumption. In the latter embodiment, it is possible to have multiple sensing signal transmissions 411 during each phase that the transparency current 401 is above the saturation level 420. However, for the present invention, saturation is not required because of the application to non-magnitizable materials. The discussion of saturation is provided for completeness. Illustrated schematicly as an apparatus in FIG. 3 and conceptually in FIG. 4, the higher frequency sensing signal 411 may be generated by a transmitter, comprised of a smaller coil 300 of conductive material, powered by alternating current and at a controlled frequency.

In FIG. 4, the high frequency sensing signal 411 is illustrated being pulsed at less than 0.5 millisecond rates. If the lower frequency transparency current 401 generated by a larger coil 551 (See FIG. 6), is pulsed or activated "on" for 10 milliseconds 430, there is sufficient time for twenty sensing signals (e.g., with a wavelength of only 0.5 millisecond) to go out to a near object and take 10 wavelengths of measurements during the "on" pulse of the transparency current. During this 10 millisecond pulse, the transparency current will exceed the saturation energy level 420. The higher frequency signal 411 from the transmitter coil 300 is being pulsed at a 0.5 millisecond rate so that 20 sensing signals will be available during a 10 millisecond pulse of the transparency signal 401.

Figure 5:
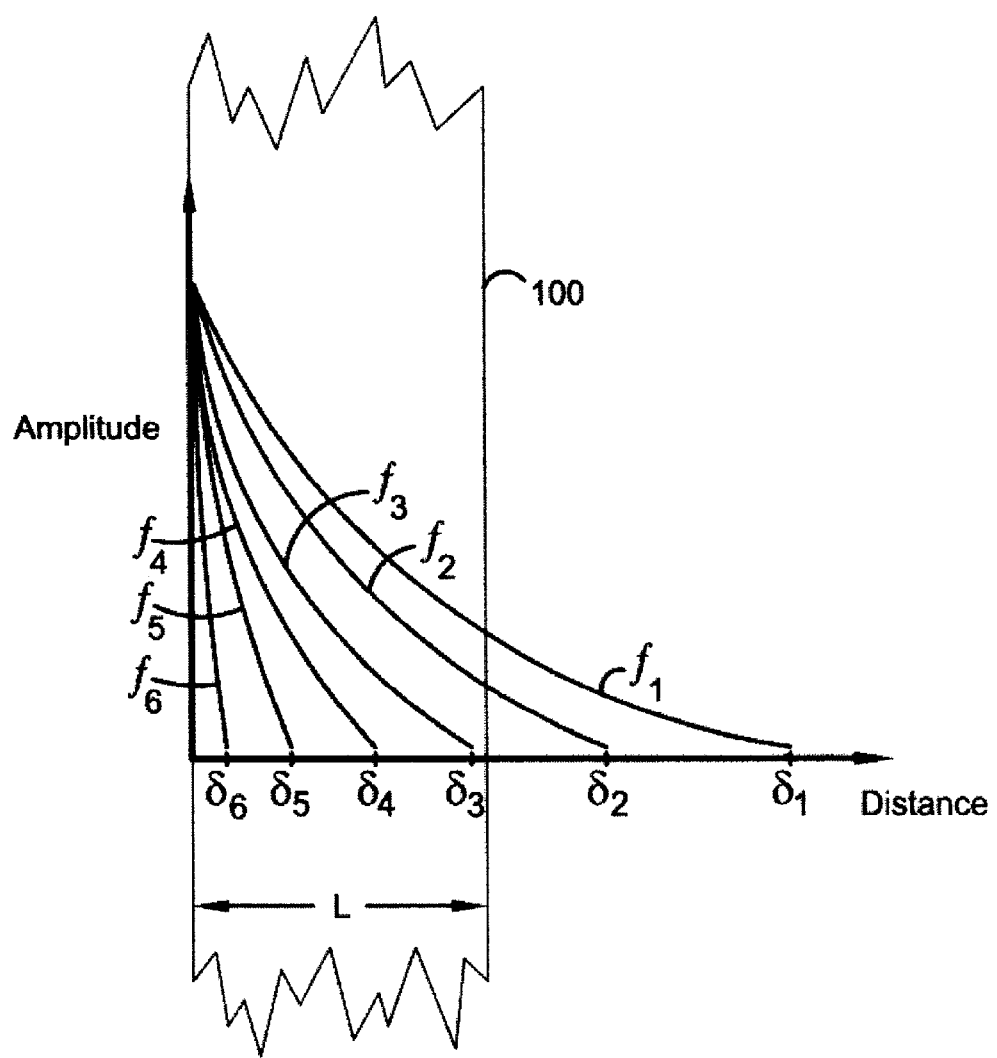
FIG. 5 illustrates the relationship between signal frequency and penetration depth for a cross-section of a material with a conductivity, a permeability and several imposed frequencies, $f_x$, for the present invention.

FIG. 5 illustrates the relationship between signal frequency and penetration depth for a cross-section of a material with a conductivity, a permeability and several imposed frequencies, $f_x$, for the present invention. For a wave of constant amplitude and varying frequency $f_x$, and a material with the same permeability and conductivity, it is known by skin depth theory that a lower frequency penetrates deeper than a higher frequency. Therefore, one can find an optimum frequency range that can characterize the material conductivity. For constant length L and varying frequencies $f_x$, the penetration depth δ is:

$$\delta = \left(\frac{1}{e}\right) L$$

and $$\delta = \frac{1}{\sqrt{\sigma \mu_r \mu_o f}}$$

where  δ = penetration depth, f = frequency, $\mu_r$ = relative permeability, and $\mu_o$ = absolute permeability.

In FIG. 5, the relationship of frequencies is:

$f_6 > f_5 > f_4 > f_3 > f_2 > f_1$.

Figure 6:
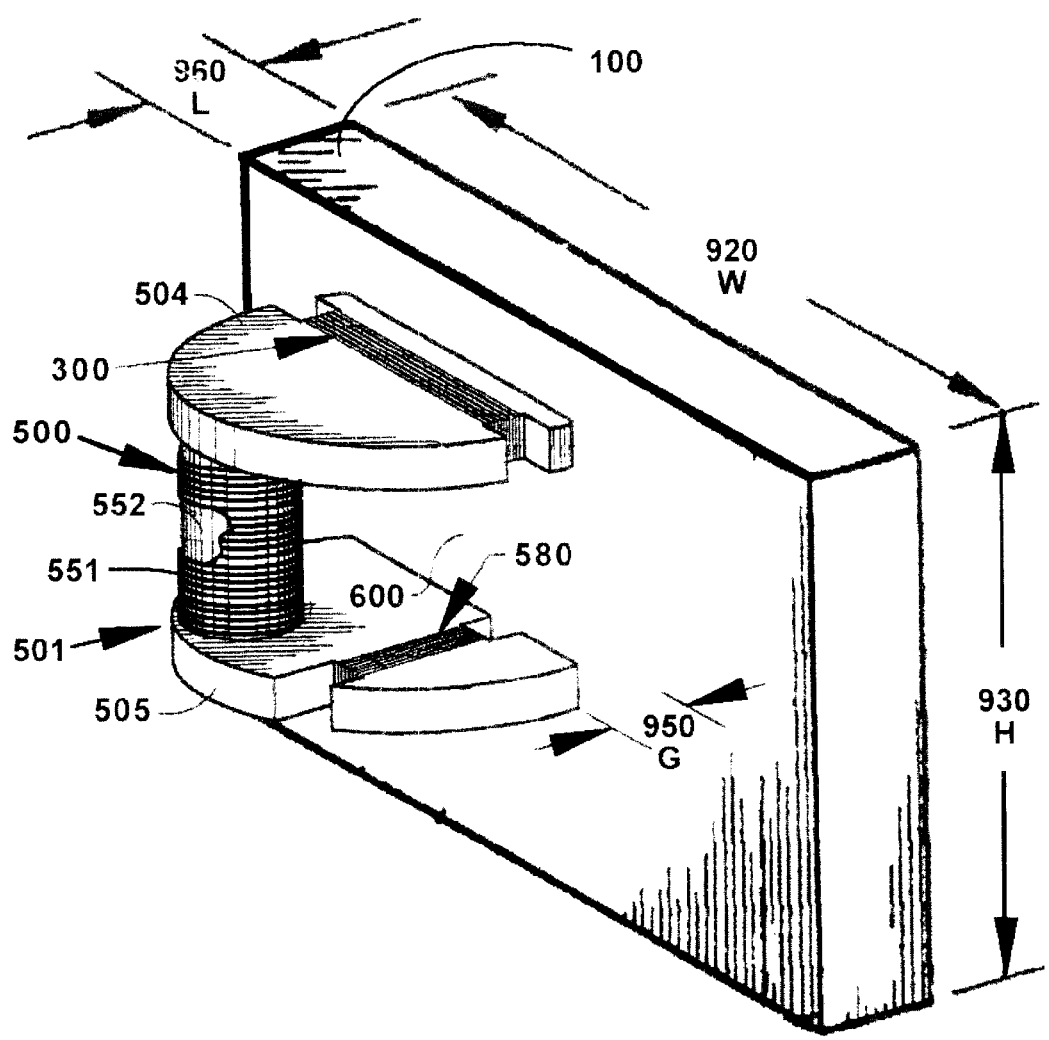
FIG. 6 illustrates one embodiment of a magnetic transparency generator used to saturate and generate the transparency current required in practicing the present invention.

FIG. 6 illustrates one embodiment of a magnetic transparency generator 500 used to saturate and generate the transparency current required in practicing the present invention. The magnetic transparency generator 500 provides for containing flux lines to completely saturate the intended barrier material 100 volume region. Also, FIG. 4 illustrates one embodiment of the flux circuit core 501 for use with the present invention. The flux circuit core 501 comprises a top flange 504, a bottom flange 505 and a core 552. The core 552, upon which the coils of the electromagnet are wrapped, is located between the top flange 504 and bottom flange 505. The tank wall comprises the barrier material 100. The complete magnetic transparency generator 500 incorporates the flux circuit core 501 for providing a transparent volume region that is illustrated having a width W 920, a height H 930 and a thickness L 960. The barrier volume region may be termed the target material. It is appreciated that the transmitter coils 300, the receiver coils 580 and the transparency coil 551 are in positions of geometric nulling with respect to the magnetic transparency generator 500 illustrated.

Figure 6A:
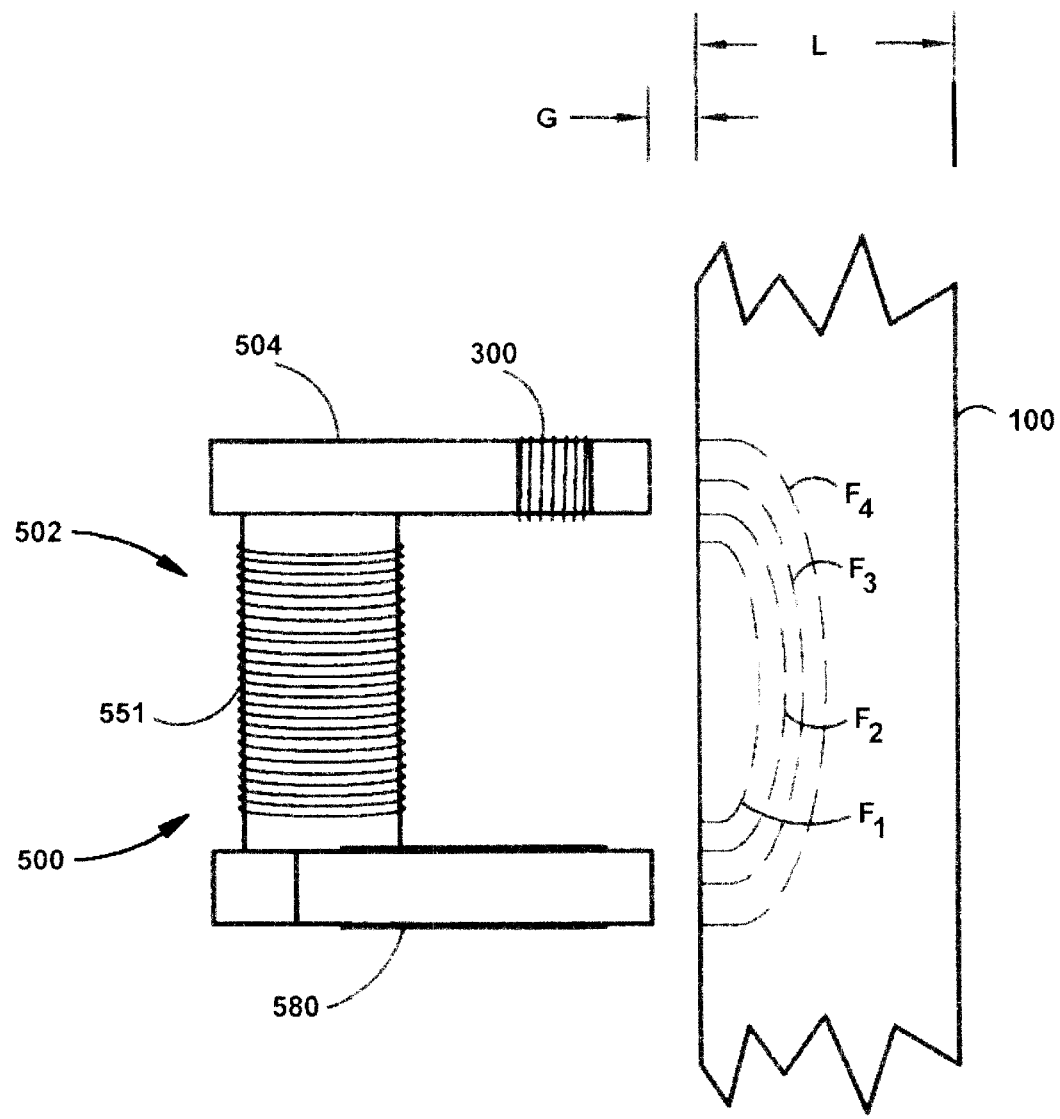

FIG. 6A illustrates one embodiment of the magnetic circuit 502 for use with the present invention. The magnetic circuit 502 comprises a saturation coil 551, a transmitter coil 300, a receiver coil 580 and a barrier material 100. A magnetic transparency generator 500 comprises the saturation coil 551, the transmitter coil 300 and the receiver coil 580. The magnetic transparency generator 500 is disposed from the barrier material 100 by a gap G. The barrier material 100 has a width L. The magnetic circuit 502 operates by energizing the saturation coil 551 for saturating the barrier material 100, transmitting a sensing signal from the transmitter coil 300, and receiving a response via the receiving coil 580. The relative penetration is caused by the change in the saturation current. Thus, as the saturation current increases from $i_1$, to $i_2$, to $i_3$, to $i_4$ then the penetration depth increases from $\delta_1$, to $\delta_2$, to $\delta_3$, to $\delta_4$, respectively. FIG. 6A illustrates the incremental increase in penetration by the field lines $F_1$, $F_2$, $F_3$ and $F_4$. Also, consideration of the cross-sectional area of each component of the magnetic circuit 502 is required to assure that no component goes into total saturation for a specific power requirement necessary to drive the EM wave across the air gap G.

Figure 6B:
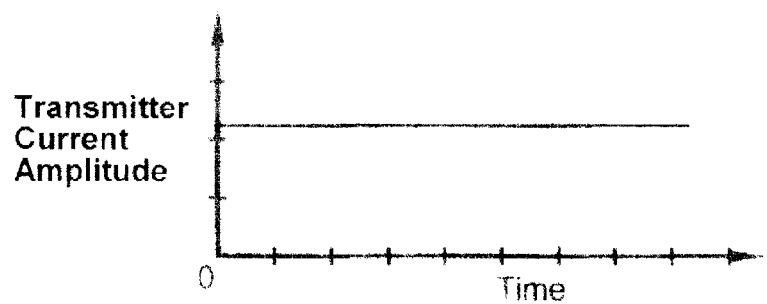
Figure 6C:
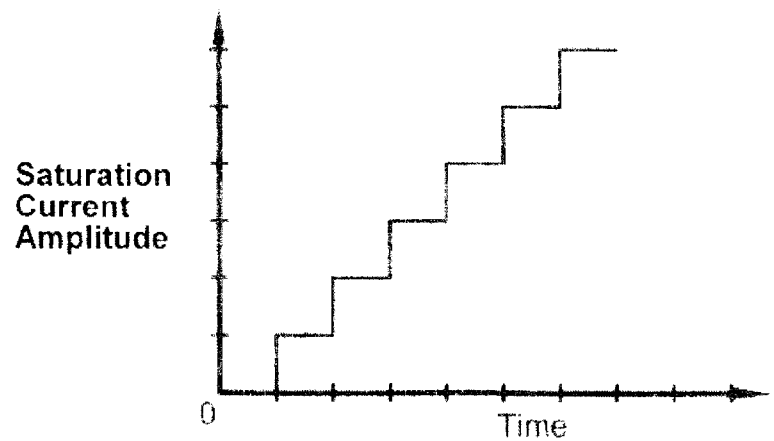
Figure 6D:
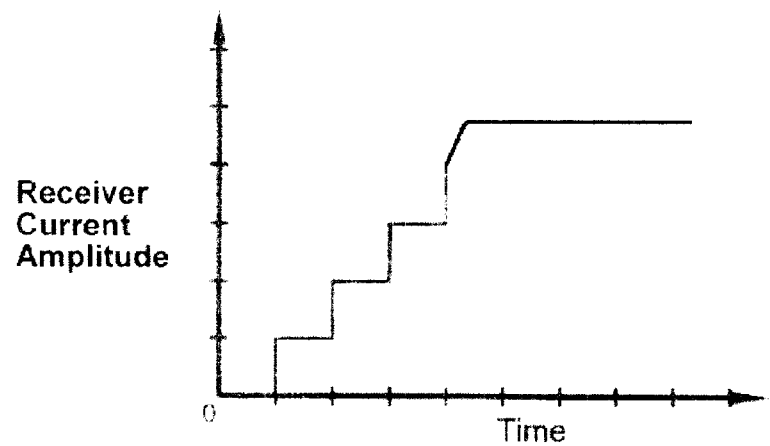

FIGS. 6B, 6C and 6D illustrate the relationship between the transmitter current amplitude, the saturation current amplitude, and the receiver current amplitude with respect to the magnetic circuit 502 illustrated in FIG. 6A. FIG. 6B illustrates that the transmitter current amplitude may be constant over time. FIG. 6C shows that the saturation current amplitude is increased as a step function over time. With the transmitter current amplitude held constant over time and the saturation current amplitude increased as a step function over time, the receiver current amplitude will increase as a step function congruent with the saturation current amplitude up to and until the barrier material is in a state of total saturation (FIG. 6D). When the barrier material is in a state of total saturation, as illustrated in FIG. 6D, the receiver current amplitude is at a maximum and cannot increase because maximum penetration has been achieved.

Figure 7:
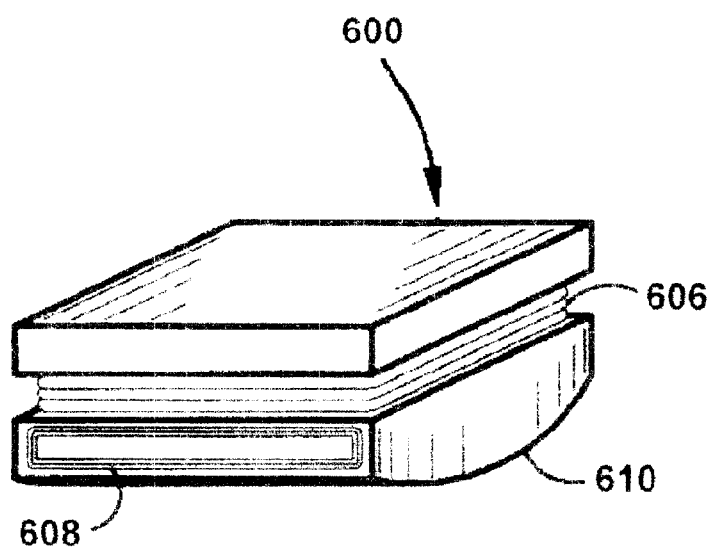
FIG. 7 illustrates one embodiment of a magnetic transparency generator 600 of the present invention.

FIG. 7 illustrates one embodiment of a magnetic transparency generator 600 of the present invention. The transmitter 606 and the receiver 608 are geometricly nulled. The displacement distance between the transmitter 606 and the receiver 608 is essentially zero. The displacement distance is essentially zero because of the close configuration of the transmitter 606 and the receiver 608. The intensity of the frequencies received will show the material thickness. For example, if all the higher frequencies are attenuated, the material is thick. If all the high frequencies are detected with little attenuation of the low frequencies, the material is thin. For a given power, the displacement distance between the transmitter 606 and the receiver 608 determines the resolution of the thickness measurement. The resolution effects the size of the defect measurable.

Figure 8:
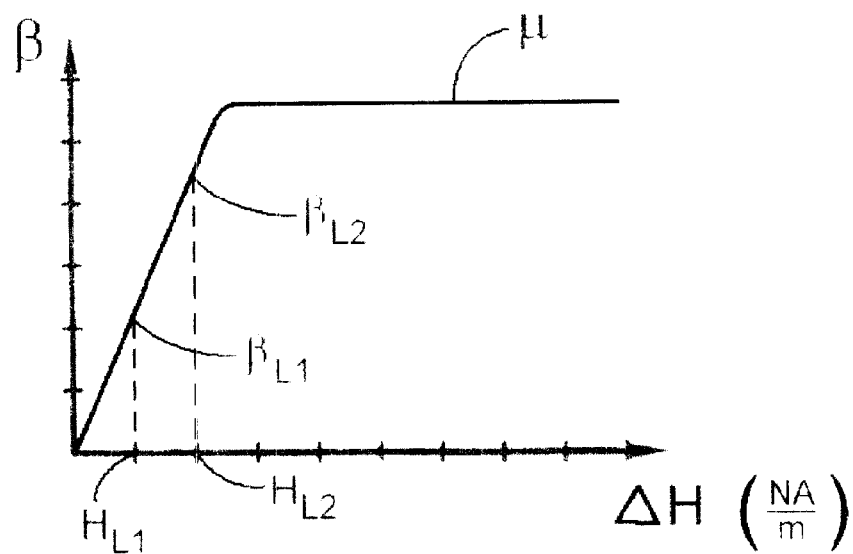
FIG. 8 illustrates the relationship between the flux field $\beta$ and the change in H ($\Delta$H) in ampere-turns/meters.

FIG. 8 illustrates the relationship between the flux field β and the change in H (ΔH) in ampere-turns/meters. The permeability μ is plotted. For the relationship between the flux field β and ΔH, the function defining the permeability μ remains the same. Although the function defining the permeability μ remains the same, the value of ΔH for thinner materials moves up the curve faster. Thus, incremental changes in H create a faster advancement up the permeability curve toward saturation. For example, a given $H_{L1}$ corresponds to the value of $β_{L1}$ and a corresponding $H_{L2}$ corresponds to the value of $β_{L2}$. Thus, the value for L2 moves faster up the permeability μ curve than the value for L1.

Figure 9:
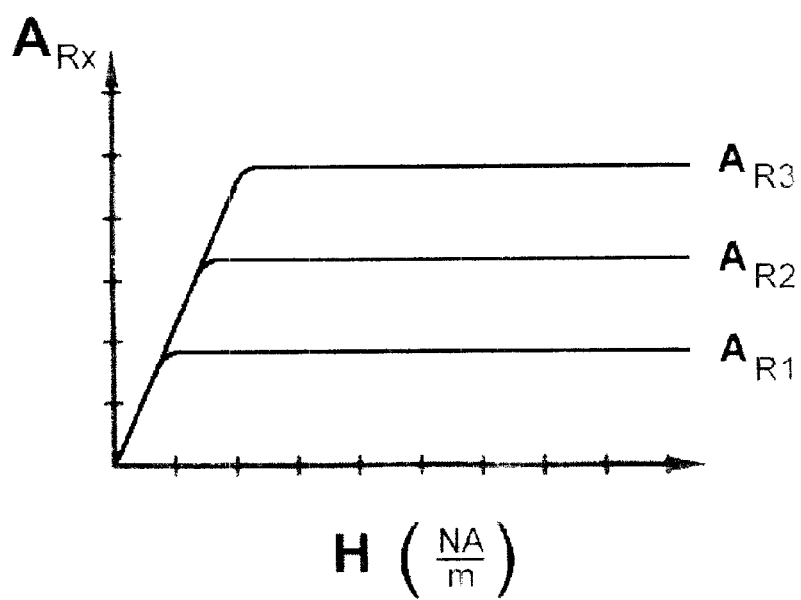
FIG. 9 illustrates the relationship between the receiver amplitude $A_{Rx}$ and H in ampere-turns/meters.

FIG. 9 illustrates the relationship between the receiver amplitude $A_{Rx}$ and H in ampere-turns/meters. As in FIG. 8, the slope of the curve in FIG. 9 is related to the permeability μ. However, the receiver amplitude $A_{Rx}$ reaches a different maximum value depending on the thickness of the material. For thinner materials, the receiver amplitude $A_{Rx}$ reaches its maximum value at a lower amplitude $A_{Rx}$. For thicker materials, the receiver amplitude $A_{Rx}$ reaches its maximum value at a higher amplitude $A_{Rx}$. FIG. 9 illustrates a thinner material having a maximum at $A_{R1}$, a thicker material having a maximum at $A_{R3}$, and an intermediate thickness material having a maximum at $A_{R2}$.

Figure 10A:
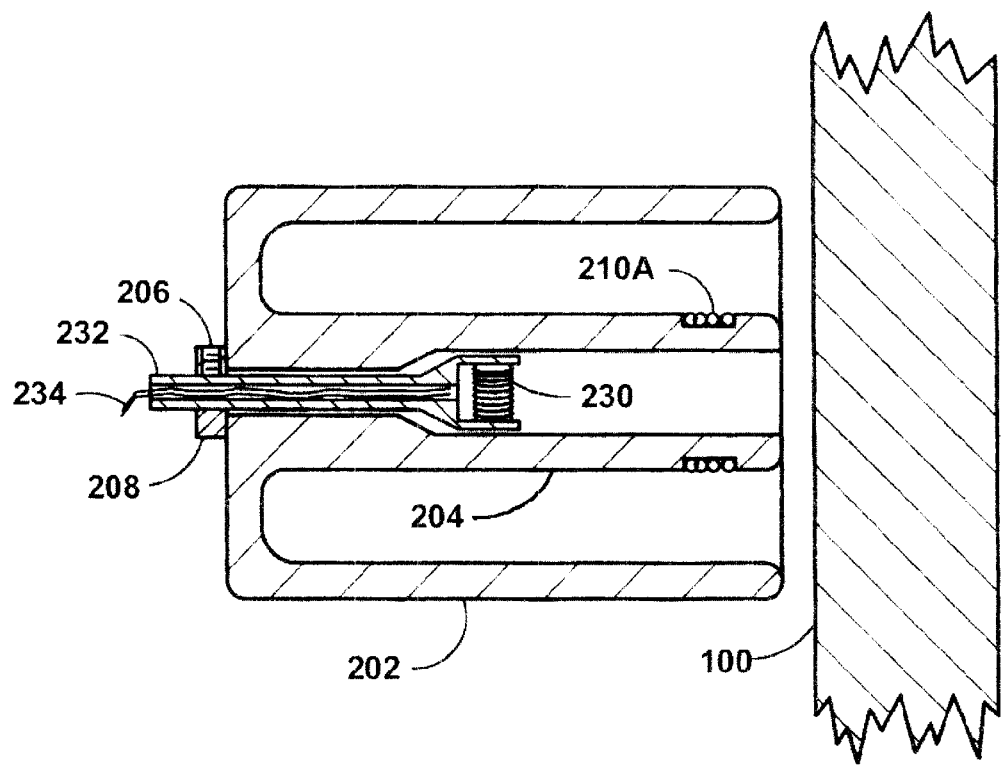
FIG. 10A illustrates an embodiment of a magnetic transparency generator used to generate a transparency with respect to a material for practicing the present invention.

FIG. 10A illustrates an embodiment of a magnetic transparency generator 200 used to generate a transparency with respect to a material 100 for practicing the present invention. A transmitter coil 210A is disposed at the remote end of the outside diameter of an inner cylindrical portion 204 of the magnetic transparency generator 200. A saturation coil 220 is disposed at the inner end of the outside diameter of the inner cylindrical portion 204 of the magnetic transparency generator 200. A receiver coil 230 is disposed within the inside diameter of the inner cylindrical portion 204 of the magnetic transparency generator 200. The receiver coil 230 can be located at different positions using a shaft 232 which telescopes within the inside diameter of the inner cylindrical portion 204 of the magnetic transparency generator 200. The telescoping shaft 232 can also rotate using a set-screw adjustment 206 and a set-screw housing 208. Also, wiring 234 can be channelled through the shaft 232.

Figure 10B:
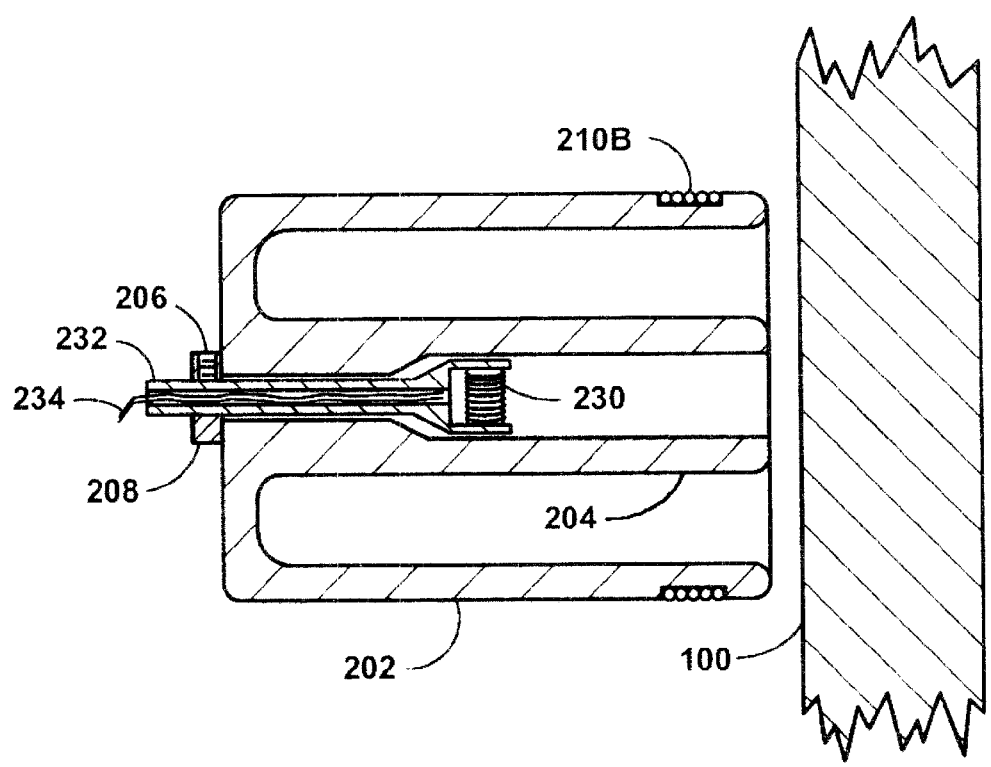
FIG. 10B illustrates another embodiment of a magnetic transparency generator used to generate a transparency with respect to a material for practicing the present invention.

FIG. 10B illustrates another embodiment of a magnetic transparency generator 200 used to generate a transparency with respect to a material 100 for practicing the present invention. A transmitter coil 210B is disposed at the remote end of the of the outside diameter of an outer cylindrical portion 202 of the magnetic transparency generator 200. A saturation coil 220 is disposed along the outside diameter of an inner cylindrical portion 204 of the magnetic transparency generator 200. A receiver coil 230 is disposed within the inside diameter of the inner cylindrical portion 204 of the magnetic transparency generator 200. The receiver coil 230 can be located at different positions using a shaft 232 which telescopes within the inside diameter of the inner cylindrical portion 204. The telescoping shaft 232 can also rotate using a set-screw adjustment 206 and a set-screw housing 208. Also, wiring 234 can be channelled through the shaft 232.

Figure 11:
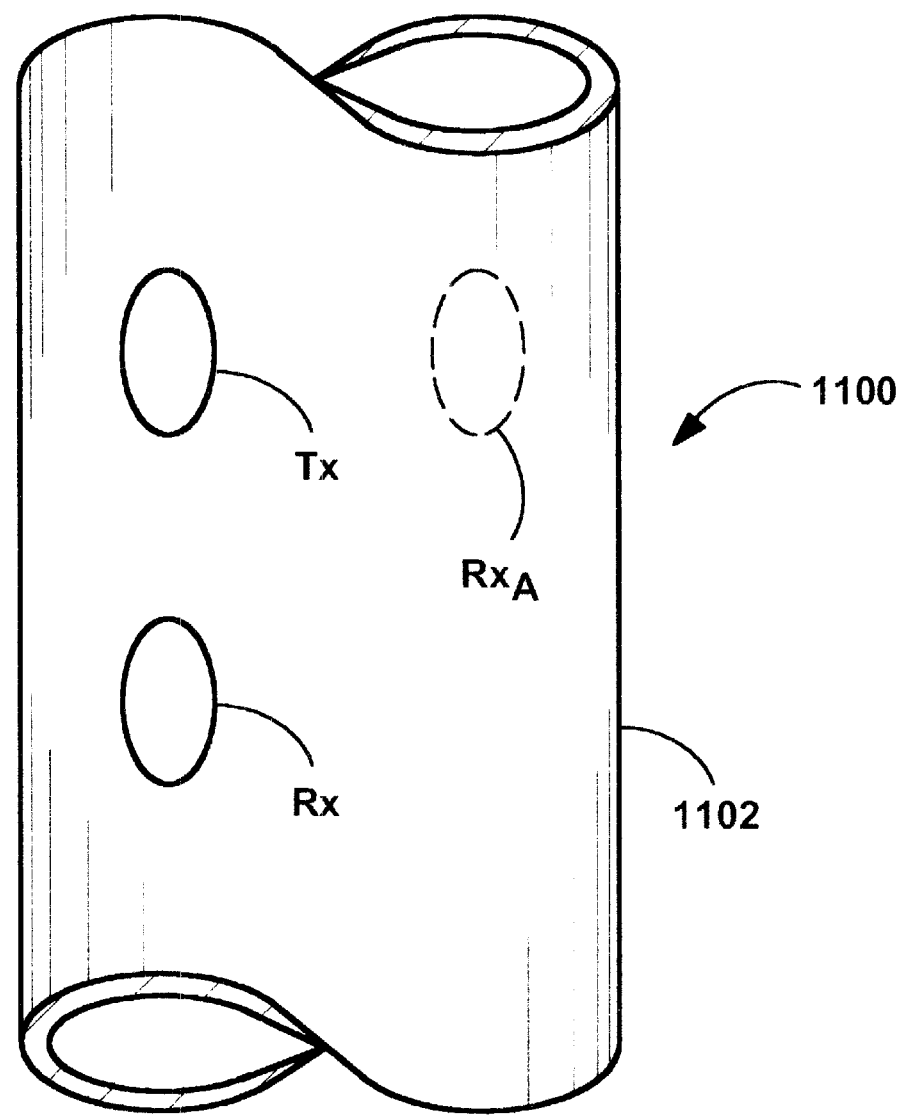
FIG. 11 illustrates a bistatic transmitter/receiver configuration 1100 used in practicing the present invention.

FIG. 11 illustrates a bistatic transmitter/receiver configuration 1100 used in practicing the present invention. The bistatic transmitter/receiver configuration 1100 maybe used to penetrate from the inside through to the outside or from the outside through to the inside of a container 1102. The container 1102 can be comprised of flat walled sides or cylindrical shaped object, e.g., a pipe or the like made of any non-ferromagnetic material. Non-ferromagnetic materials are, for example, stainless steel, aluminum, bronze, copper, fiberglass or other non-magnetizable material. FIG. 11 illustrates a single transmitter Tx and a single receiver Rx disposed along the container 1102. An alternate position for the single receiver Rx is also illustrated in FIG. 11. The alignment of the receiver Rx for use with the bistatic transmitter/receiver configuration 1100 of FIG. 11 is axially radial.

Figure 12A:
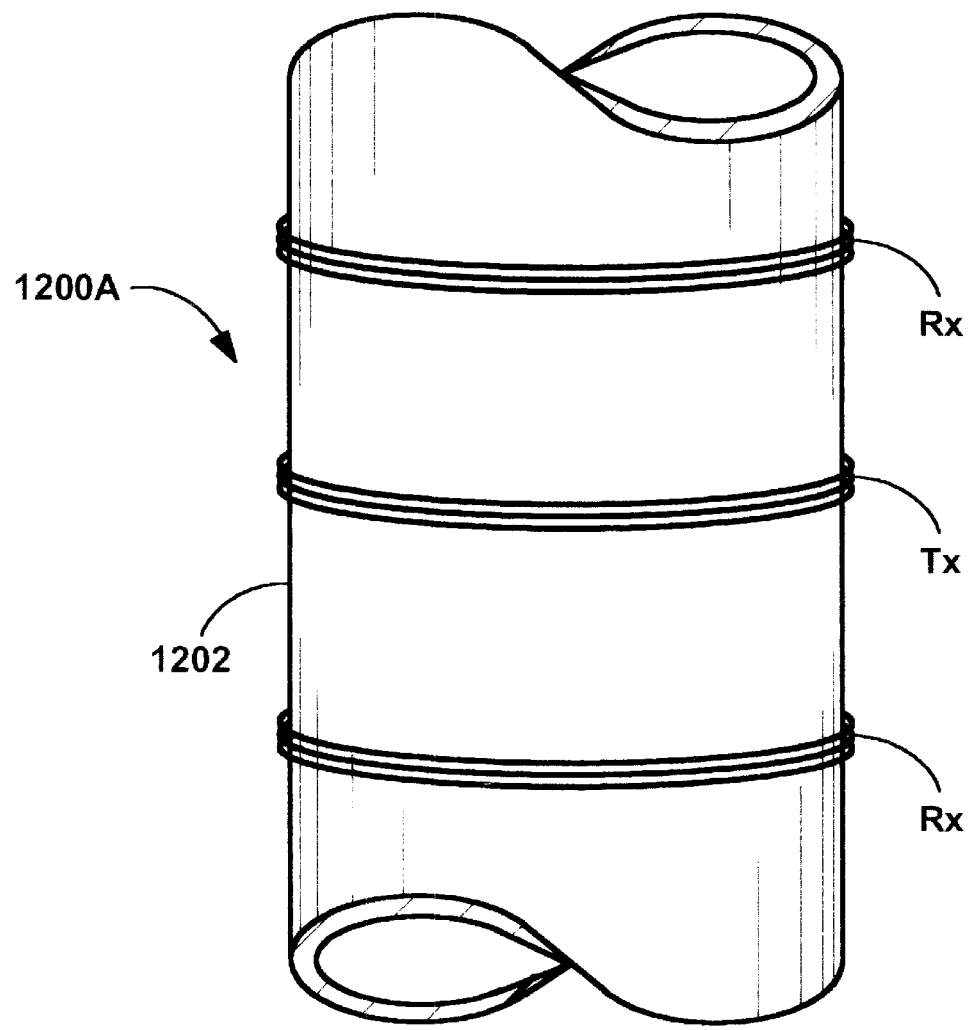
FIGS. 12A, 12B and 12C illustrate examples of tristatic transmitter/receiver configurations as practiced with the present invention.
Figure 12B:
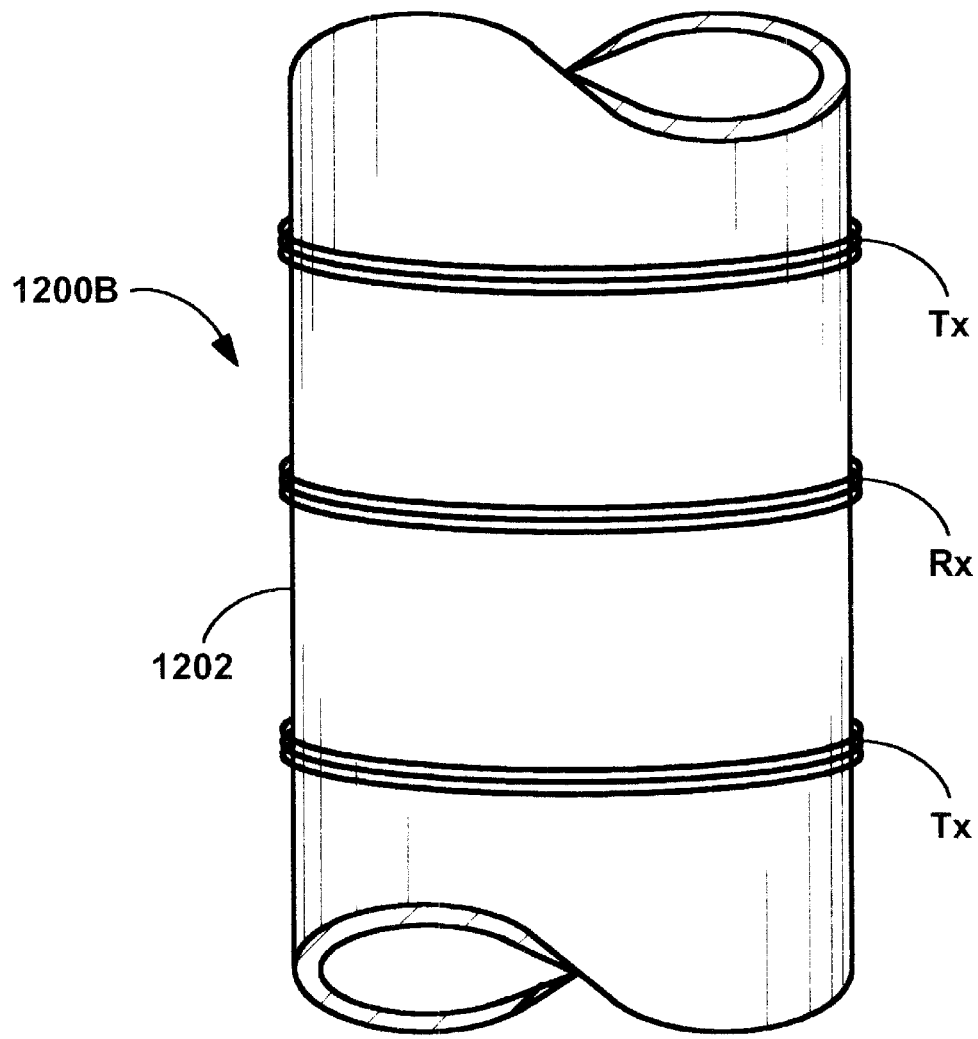
Figure 12C:
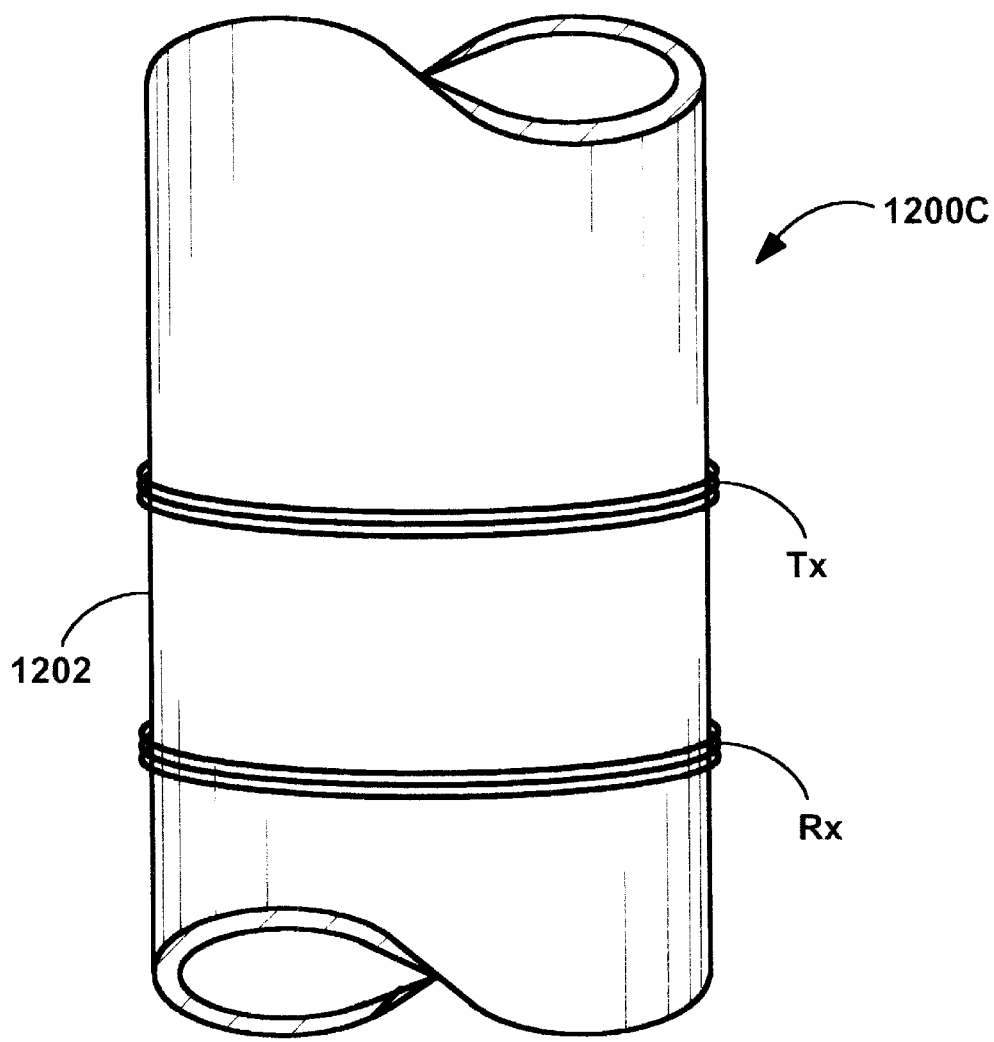

FIGS. 12A, 12B and 12C illustrate examples of tristatic transmitter/receiver configurations 1200A, 1200B, 1200C, respectively, as practiced with the present invention. FIG. 12A illustrates a single transmitter Tx and two receivers Rx. FIG. 12B illustrates a transmitter/receiver configuration 1200B using two transmitters Tx and one receiver Rx. FIG. 12C is a bistatic embodiment 1200C using a transmitter Tx and a receiver Rx. The type of container 1202 is made of non-ferromagnetic material. The receivers Rx and transmitters Tx are wrapped around the pipe or container 1202. The receivers Rx and transmitters Tx can be disposed inside the container 1202 to penetrate through to the outside. Alternately, the transmitters Tx and receivers Rx can be disposed outside of the container 1202 to penetrate to the inside.

Figure 13A:
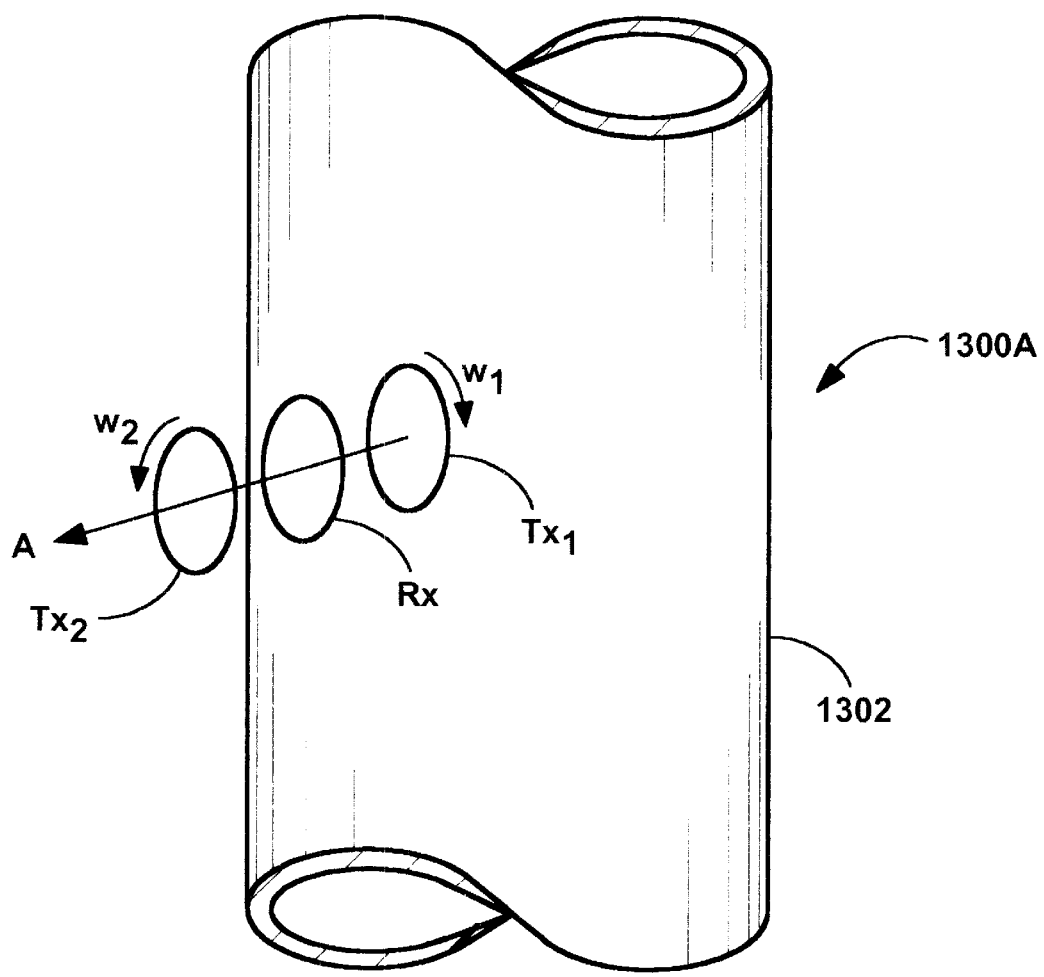
FIGS. 13A, 13B, 13C, 13D and 13E are illustrations and graph of an axially symmetric configuration of transmitters and receivers such that the receiver coils are centered along the same axis.

FIGS. 13A, 13B, 13C and 13D are illustrations of an axially symmetric configuration of transmitters Tx and receivers Rx such that the receiver coils are centered along the same axis A. FIG. 13A illustrates an axially symmetric configuration 1300A of two transmitters $Tx_1$, $Tx_2$ and a receiver Rx disposed there between. The transmitter/receiver configuration 1300A is in operative association with a pipe, container or wall 1302. The pipe, container or wall 1302 is made from non-ferromagnetic material. The transmitters $Tx_1$, $Tx_2$ are "bucked." The transmitters $Tx_1$, $Tx_2$ being bucked requires that the coils associated with the transmitters $Tx_1$, $Tx_2$ are wound in opposite directions. As illustrated in FIG. 13A, the coils for $Tx_1$ are wound in a clockwise direction $w_1$. The coil associated with the second transmitter $Tx_2$ is wound in a counter clockwise direction $w_2$. The coil for the receiver Rx can be wound in either direction. When the transmitters $Tx_1$, $Tx_2$ are bucked, i.e. wound in opposite directions, the field lines generated are described by the right thumb rule. Thus, bucking provides a canceling of the respective field lines associated with the bucked transmitters $Tx_1$, $Tx_2$. In the transmitter/receiver configuration 1300A illustrated in FIG. 13A, the receiver Rx must be between the two transmitters $Tx_1$, $Tx_2$.

Figure 13B:
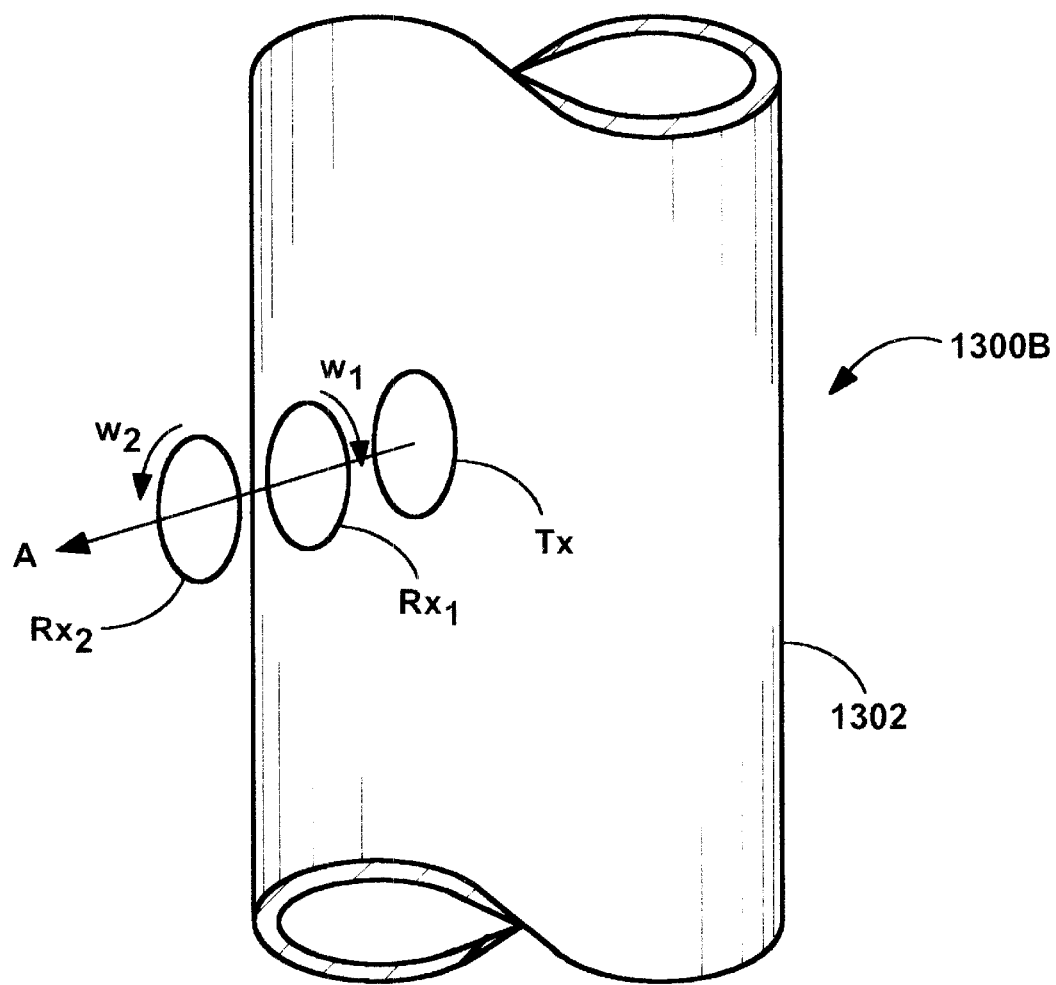

FIG. 13B is another embodiment of a transmitter/receiver configuration 1300B which is axially symmetric. A first receiver $Rx_1$ is disposed adjacent a second receiver $Rx_2$. A transmitter Tx is disposed remote from the two receivers $Rx_1$, $Rx_2$ such that the transmitter Tx is not between the receivers $Rx_1$, $Rx_2$. The receivers $Rx_1$, $Rx_2$ are bucked, i.e. wound in opposite directions. The bucked receivers provide that field lines generated are canceling. The transmitter/receiver configuration 1300B in FIG. 13B, having two receivers $Rx_1$, $Rx_2$, is functional with the transmitter Tx placed anywhere along the central axis of the transmitter/receiver configuration 1300B. Further, as with FIG. 13A, the embodiment of the transmitter/receiver configuration 1300B illustrated in FIG. 13B provides that the transmitter/receiver configuration 1300B maybe placed inside the wall to penetrate to the outside. Alternately, the transmitter/receiver configuration 1300B can be placed outside of the wall to penetrate to the inside. The receiver $Rx_1$ is illustrated with its coil wound in a clockwise direction $w_1$. The receiver $Rx_2$ is illustrated with coil wound in a counter clockwise orientation $w_2$.

Figure 13C:
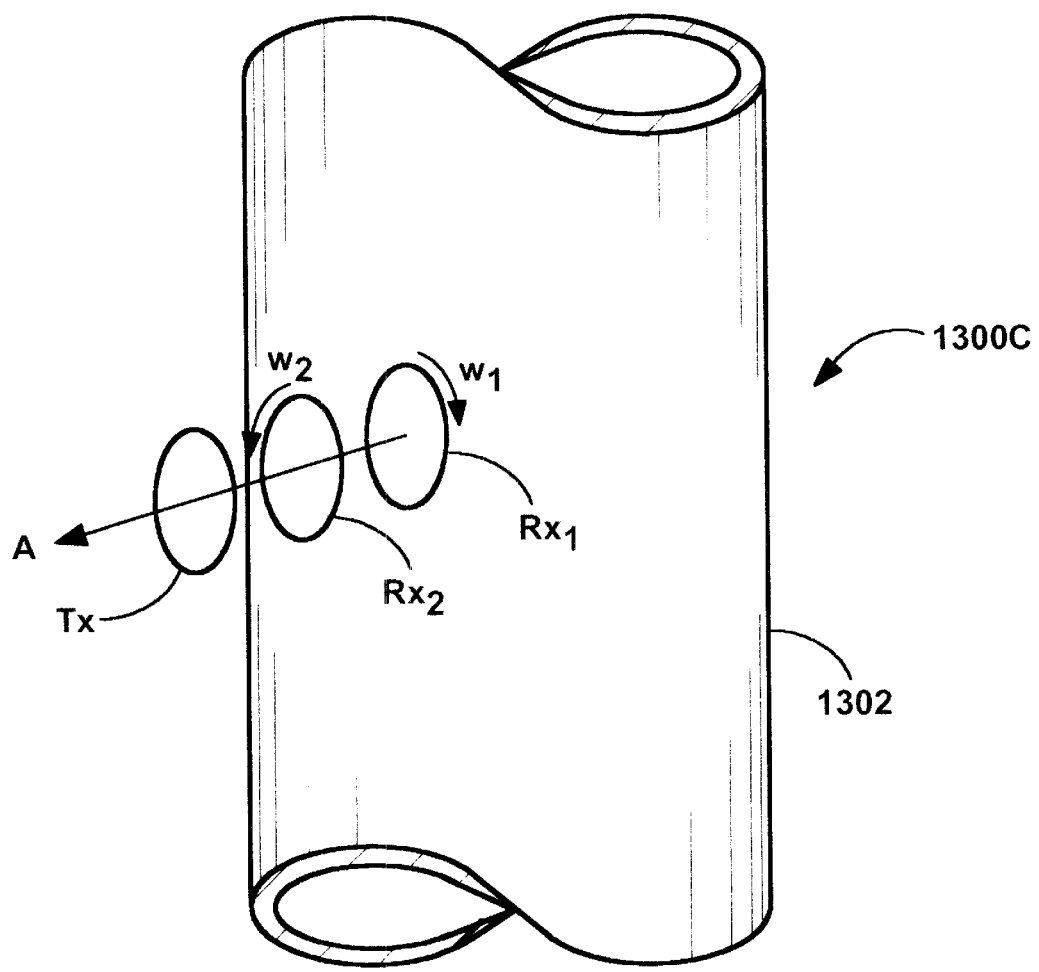

FIG. 13C is another embodiment of the present invention illustrating a transmitter/receiver configuration 1300C that is axially symmetric. A pair of receivers $Rx_1$, $Rx_2$ are disposed adjacent to pipe, container or wall 1302 oriented so that the receivers $Rx_1$, $Rx_2$ are axially configured along a central axis A. A transmitter Tx is disposed remote from the receivers $Rx_1$, $Rx_2$ which are remote from the pipe 1302. The receivers $Rx_1$, $Rx_2$ are bucked. The first receiver $Rx_1$ is wound in a clockwise direction $w_1$, and the second receiver $Rx_2$ is wound in a counter clockwise $w_2$. The pipe 1302 is made of a non-ferromagnetic material. The transmitter/receiver configuration 1300C maybe placed on the outside to penetrate to the inside, or alternately placed inside to penetrate to the outside.

Figure 13D:
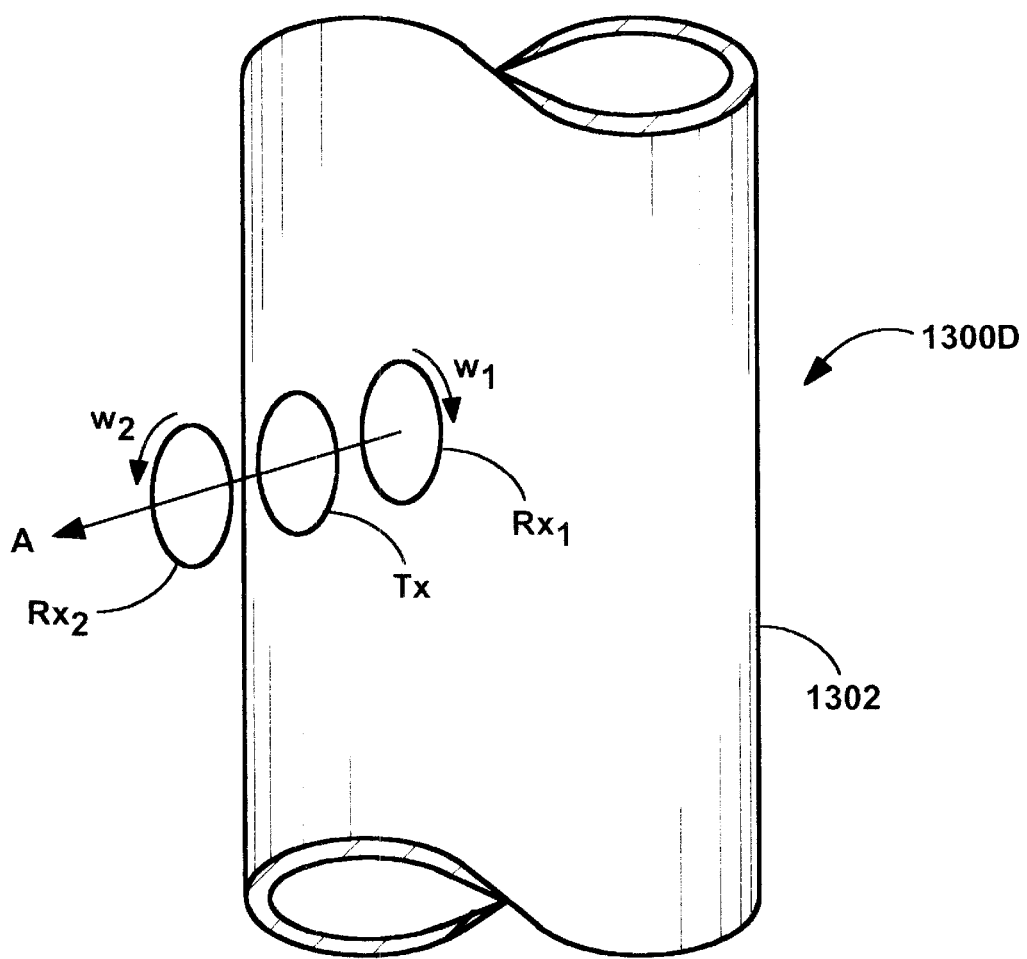

FIG. 13D is another illustration of a receiver/transmitter configuration 1300D which is actually symmetric. A first receiver $Rx_1$ is disposed adjacent a pipe, container or wall 1302. The pipe container or wall 1302 is made from a non-ferromagnetic material. A second receiver $Rx_2$ is disposed remote from the first receiver $Rx_1$ in the wall 1302. Between the first receiver $Rx_1$ and the second receiver $Rx_2$, a transmitter Tx is disposed. The receivers $Rx_1$, $Rx_2$ are also bucked. FIG. 13D illustrates the first receiver $Rx_1$ being wound in a clockwise direction $w_1$, and the second receiver $Rx_2$ being wound in a counter clockwise orientation $w_2$. As with the other axially symmetric configurations, the present receiver/transmitter configuration 1300D maybe placed on the outside of the wall 1302 to penetrate to the inside, or alternately, maybe placed on the inside of the wall 1302 to penetrate to the outside.

Figure 13E:
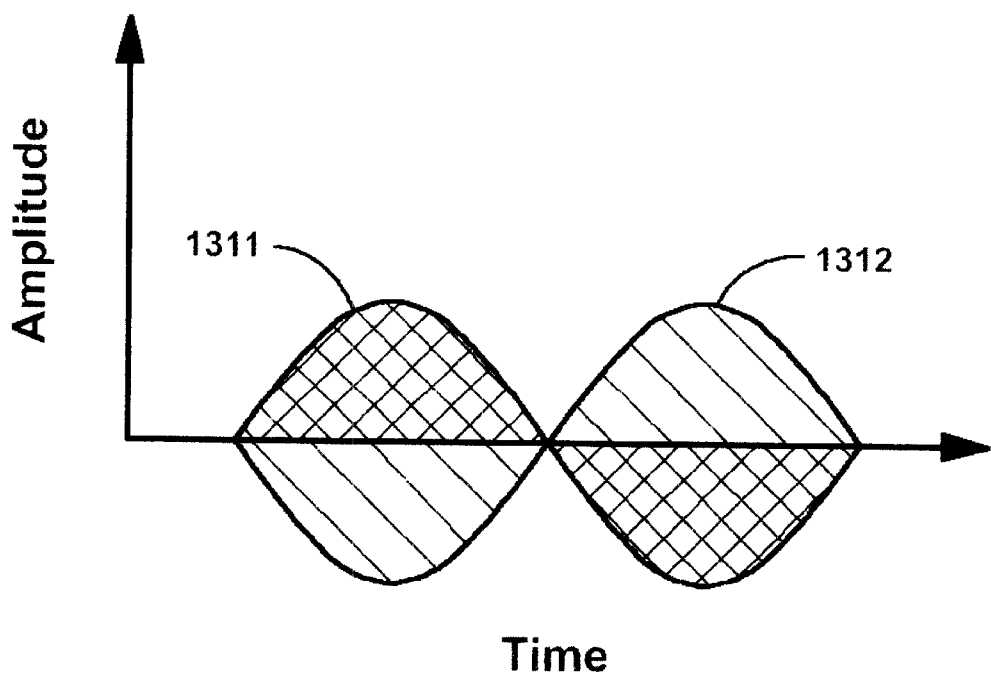

FIG. 13E is a graph of amplitude versus time illustrating the signals 1311, 1312 associated with the bucked transmitters Tx and receivers Rx illustrated in FIGS. 13A, 13B, 13C and 13D. The left cross-hatched signal 1311 is the mirror image of the right cross-hatched signal 1312 such that the bucking relationship cancels portions of the signal.

Figure 14A:
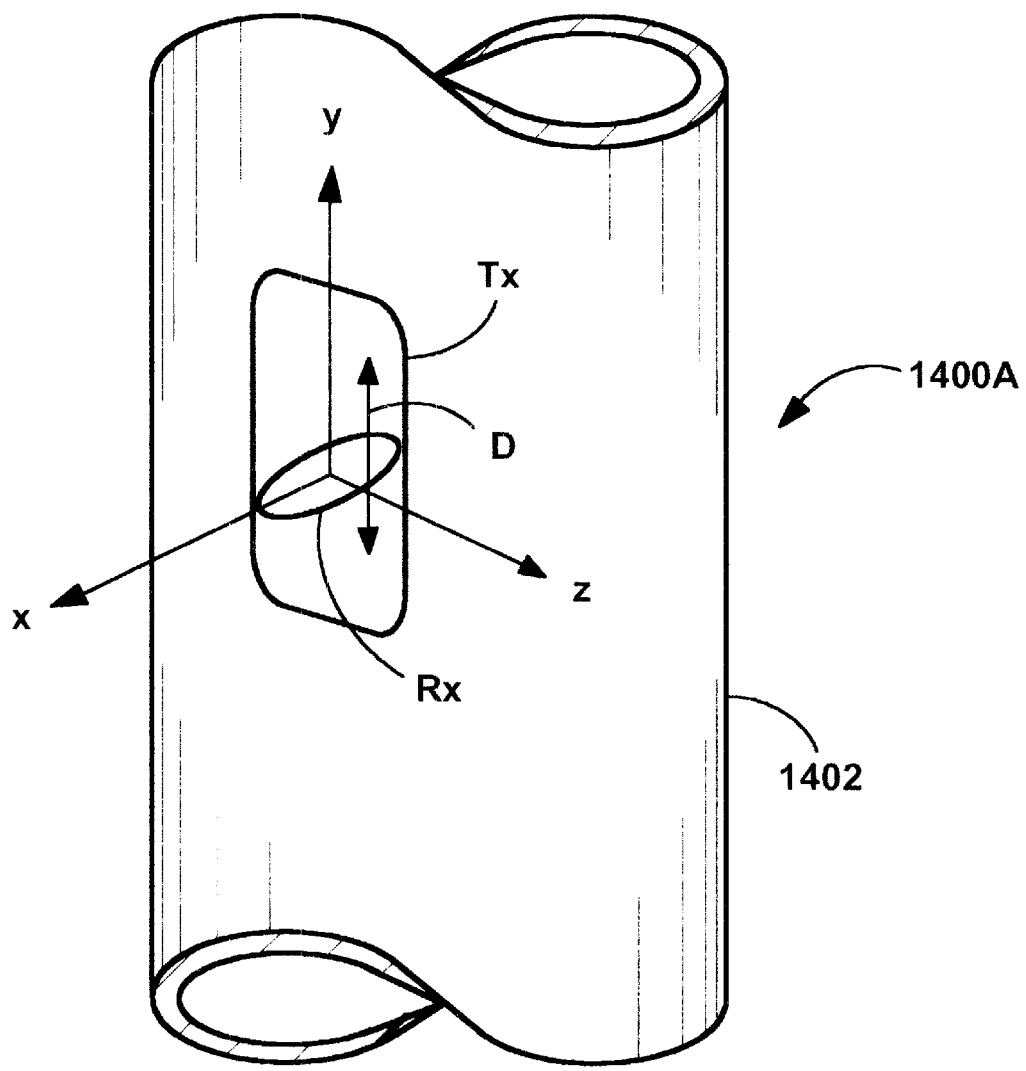
FIG. 14A illustrates an embedded transmitter/receiver configuration as practiced by the present invention.

FIG. 14A illustrates an embedded transmitter/receiver configuration 1400A as practiced by the present invention. The embedded transmitter/receiver configuration 1400A is operatively associated with a pipe, wall or container 1402. The pipe 1402 is made from a non-ferromagnetic material. A transmitter Tx is disposed in a plane that is parallel to, or alternately, tangent to, the plane of the surface of the pipe 1402. A receiver Rx is disposed in such a way as the receiver Rx is embedded within and has a 90 degree relationship with the transmitter Tx. Thus, the receiver Rx can be moveably located to multiple positions D within the transmitter Tx. More particularly, the interior receiver Rx can be moveably located within the transmitter Tx to provide an enhanced null for the best transmitter/receiver configuration 1400A for the desired application. The transmitter Tx and the receiver Rx are nulled with respect to each other. The enhanced null characteristics of the transmitter/receiver configuration 1400A illustrated in FIG. 14A provides for a way to avoid the induced characteristics of the evaluated system, which evaluated system may be a pipe, a wall, a pipe with water in it, a wall with a substance on it, an oil well casing, etc. For example, an embodiment of the present invention as illustrated in FIG. 14A can be placed next to a tank with water in the tank. The transmitter/receiver configuration 1400A is nulled with the water in the tank. If salt is added to the water, the null will be disrupted and the salinity can be determined. Another example is to null the embedded transmitter/receiver configuration 1400A illustrated in FIG. 1A away from the tank. Thereafter, moving the embedded configuration to the tank will get a change in signal with respect to the tank and what ever is in the tank. The directionality depends on the particular application being evaluated, for example, inside the pipe, outside the pipe, remote from the pipe, etc.

Figure 14B:
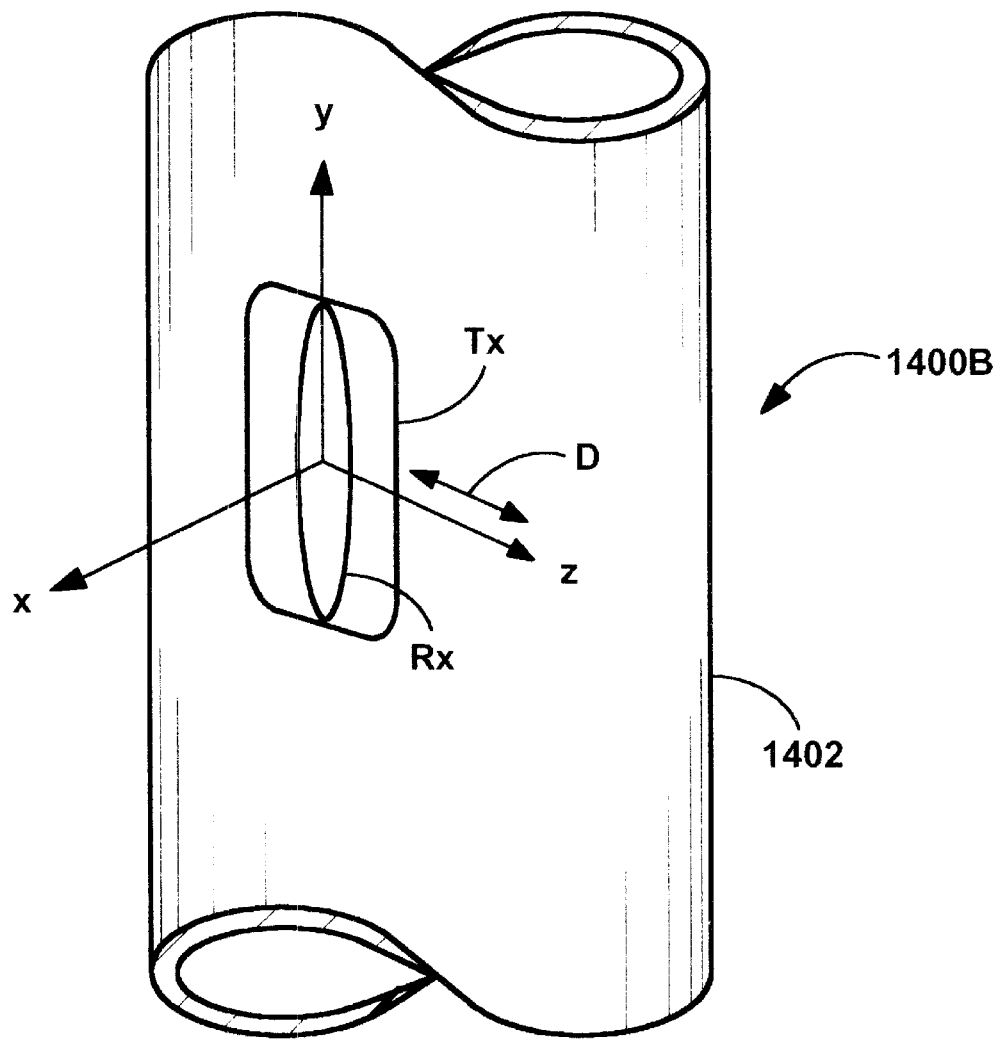
FIG. 14B is another embedded transmitter/receiver configuration as practiced by the present invention.

FIG. 14B is another embedded transmitter/receiver configuration 1400B as practiced by the present invention. The embedded transmitter/receiver configuration 1400B in FIG. 14B provides for the configuration to be operatively associated with the pipe, container or wall 1402 made from a non-ferromagnetic material. The transmitter Tx is disposed in the plane of the pipe 1402. The receiver Rx is disposed in or embedded within the transmitter Tx so is to have an orthogonal relationship with the transmitter Tx and the pipe 1402. A receiver Rx is disposed in such a way as the receiver Rx is embedded within and has a 90 degree relationship with the transmitter Tx. Thus, the receiver Rx can be moveably located to multiple positions D within the transmitter Tx. More particularly, the interior receiver Rx can be moveably located within the transmitter Tx to provide an enhanced null for the best transmitter/receiver configuration 1400B for the desired application. The transmitter Tx and the receiver Rx are nulled with respect to each other. The enhanced null characteristics of the transmitter/receiver configuration 1400A illustrated in FIG. 14A provides for a way to avoid the induced characteristics of the evaluated system, which evaluated system may be a pipe, a wall, a pipe with water in it, a wall with a substance on it, an oil well casing, etc. The transmitter/receiver embedded configuration maybe placed on the outside of the pipe to look in or alternately, placed on the inside of the pipe to look out.

Figure 15A:
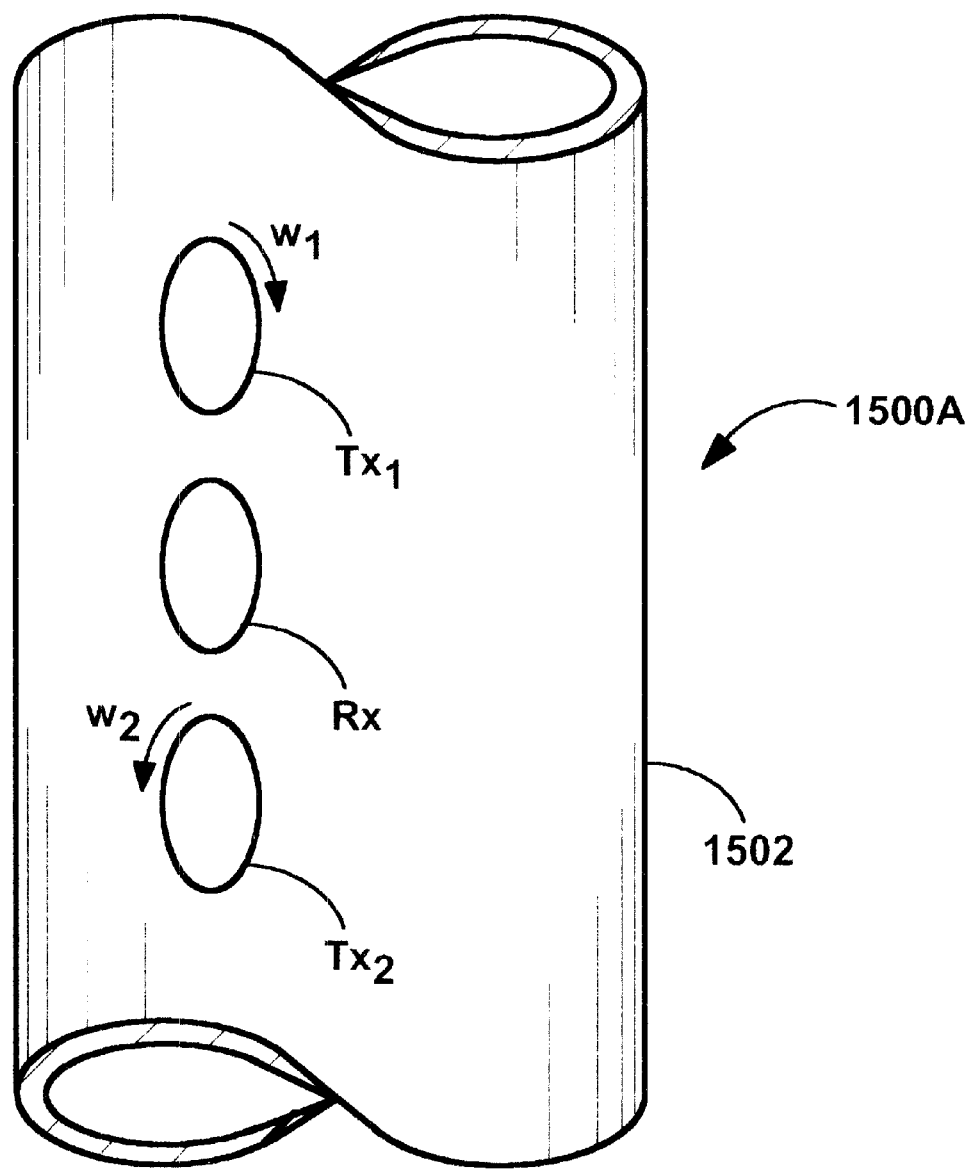
FIG. 15A is a tristatic configuration of the present invention.

FIG. 15A is a tristatic configuration 1500A of the present invention. The tristatic configuration 1500A provides for the transmitters $Tx_1$, $Tx_2$ and the receiver Rx to be on the same plane, but having different central axis. The tristatic configuration 1500A is adapted with a pipe container or wall 1502 made from non-ferromagnetic material. The transmitters $Tx_1$, $Tx_2$ are bucked. The transmitters $Tx_1$, $Tx_2$ being bucked requires that the coils associated with the transmitters $Tx_1$, $Tx_2$ are wound in opposite directions. As illustrated in FIG. 15A, the coil for $Tx_1$ is wound in a clockwise direction $w_1$. The coil associated with the second transmitter $Tx_2$ is wound in a counter clockwise direction $w_2$. The coil for the receiver Rx can be wound in either direction. The tristatic configuration 1500A maybe placed outside the pipe 1500A to penetrate inside the pipe 1500A or alternately, maybe placed inside the pipe to penetrate to the outside.

Figure 15B:
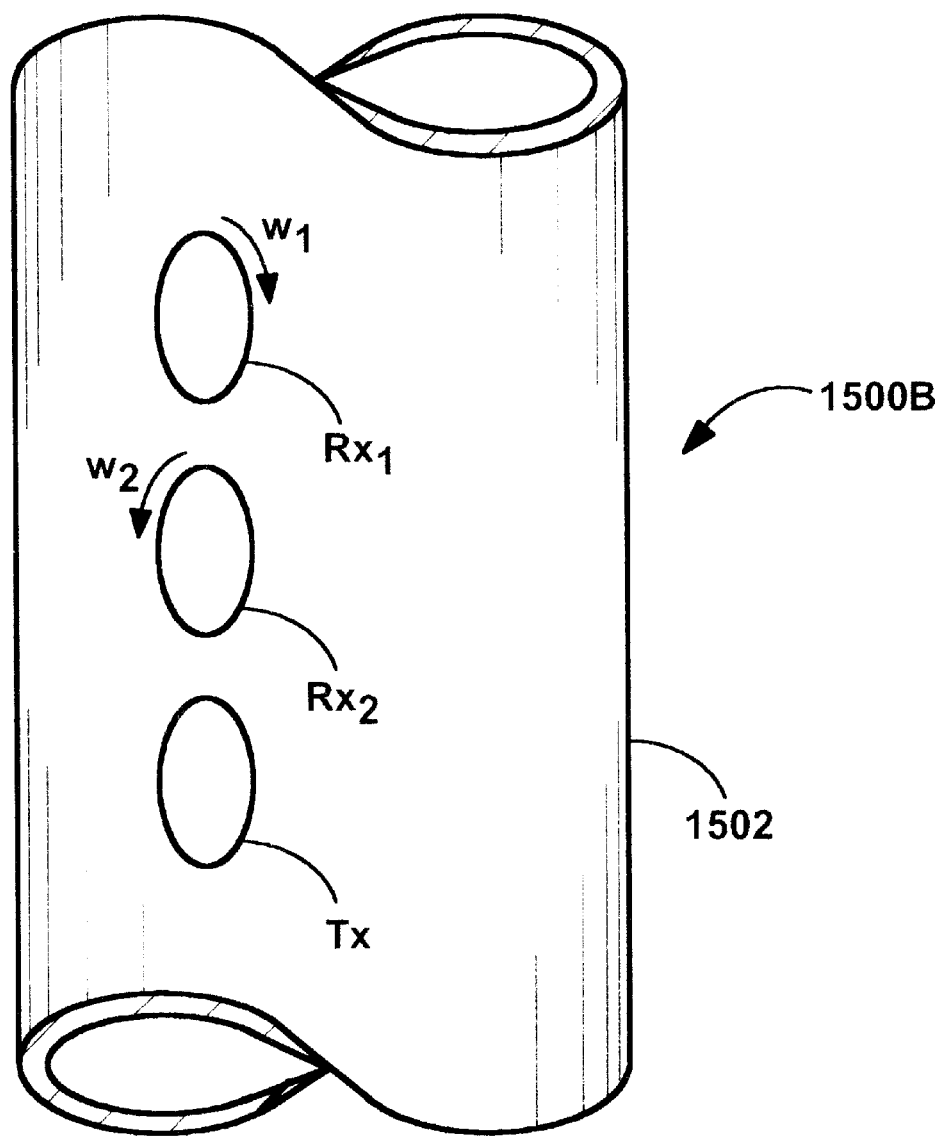
FIG. 15B is another tristatic configuration of the present invention.

FIG. 15B is another tristatic configuration 1500B of nulling with respect to the present invention. The tristatic configuration 1500B is operatively associated with the pipe container or wall 1502 made from non-ferromagnetic material. Two receivers $Rx_1$, $Rx_2$ are disposed adjacent each other along the plane of the pipe 1502. A transmitter Tx is disposed along the same plane as the receivers $Rx_1$, $Rx_2$ but having different central axis. The receivers $Rx_1$, $Rx_2$ are bucked. The receivers $Rx_1$, $Rx_2$ being bucked requires that the coils associated with the receivers $Rx_1$, $Rx_2$ are wound in opposite directions. As illustrated in FIG. 15B, the coil for receiver $Rx_1$ is wound in a clockwise direction $w_1$. The coil associated with the second receiver $Rx_2$ is wound in a counter clockwise direction $w_2$. The coil for the transmitter Tx can be wound in either direction. The tristatic configuration 1500B of FIG. 15B can be placed on the outside of the pipe 1502 for looking into the pipe, or alternately can be placed inside the pipe for looking outwardly.

Figure 16:
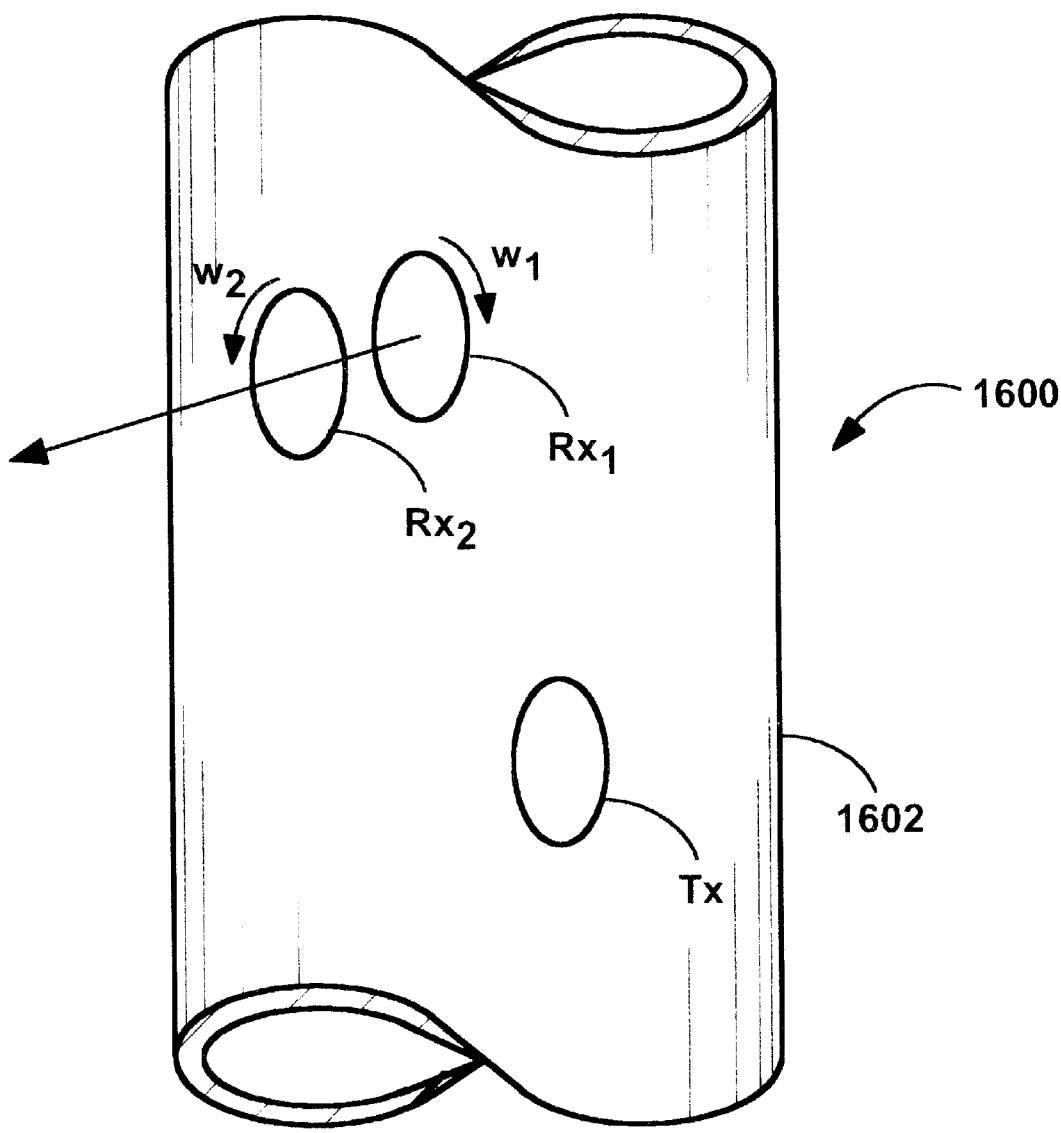
FIG. 16 is another configuration of nulling combining the axially symmetric relationships of FIGS. 13A, 13B, 13C and 13D with the static configurations illustrated in FIGS. 15A and 15B.

FIG. 16 is yet another configuration 1600 of nulling combining the axially symmetric relationships of FIGS. 13A, 13B, 13C and 13D with the static configurations illustrated in FIGS. 15A and 15B. A pair of receivers $Rx_1$, $Rx_2$ are oriented so as to be axially symmetric along an axis A. A transmitter Tx is disposed remote from the axial relationship of the receivers $Rx_1$, $Rx_2$. Similarly, the receivers $Rx_1$, $Rx_2$ can be bucked. The receivers $Rx_1$, $Rx_2$ being bucked requires that the coils associated with the receivers $Rx_1$, $Rx_2$ are wound in opposite directions. As illustrated in FIG. 16, the coil for receiver $Rx_1$ is wound in a clockwise direction $w_1$. The coil associated with the second receiver $Rx_2$ is wound in a counter clockwise direction $w_2$. The coil for the transmitter Tx can be wound in either direction. The mixed configuration 1600 can be placed on the outside of the pipe 1602 to penetrate to the inside or alternately, placed on the inside of the pipe 1602 to penetrate to the outside.

Figure 17:
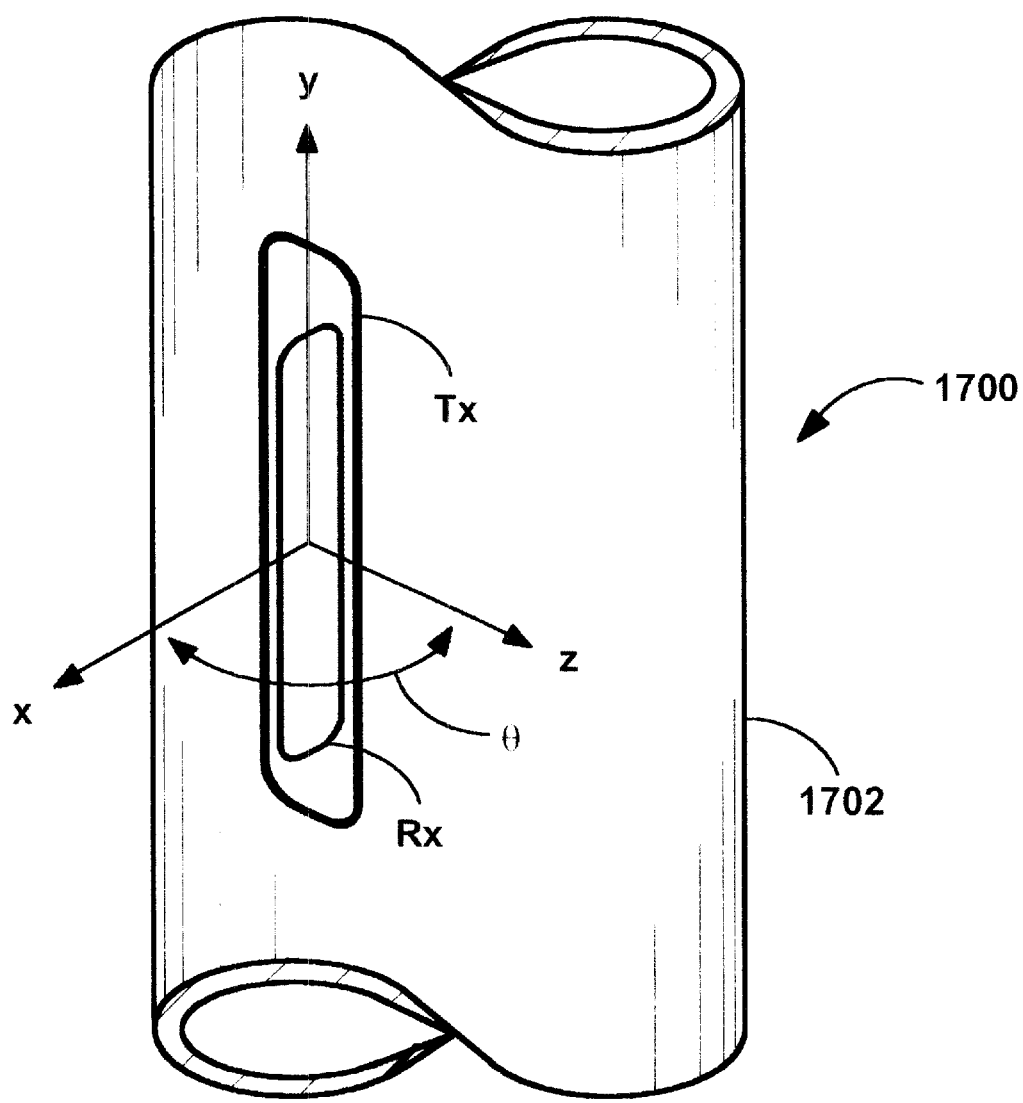
FIG. 17 is an embedded, rotating receiver/transmitter configuration as practiced by the present invention.

FIG. 17 is an embedded, rotating receiver/transmitter configuration 1700 as practiced by the present invention. The embedded rotating receiver/transmitter configuration 1700 is operatively associated with a pipe container or wall 1702 made from non-ferromagnetic material. The transmitter Tx is oriented orthogonal to the pipe, container or wall 1702. The embedded receiver Rx is disposed such that it can be rotated within the transmitter Tx. The rotating of the embedded receiver Rx provides for enhanced nulling of the embedded configuration. The embedded configuration may be placed on the inside of the pipe 1702 for examining outer regions, or alternately may be placed outside the pipe 1702 for examining the inside of the pipe. The characteristics discussed above for the other nulled configurations applies to the embedded, rotating receiver/transmitter configuration 1700 as well.

Figure 18:
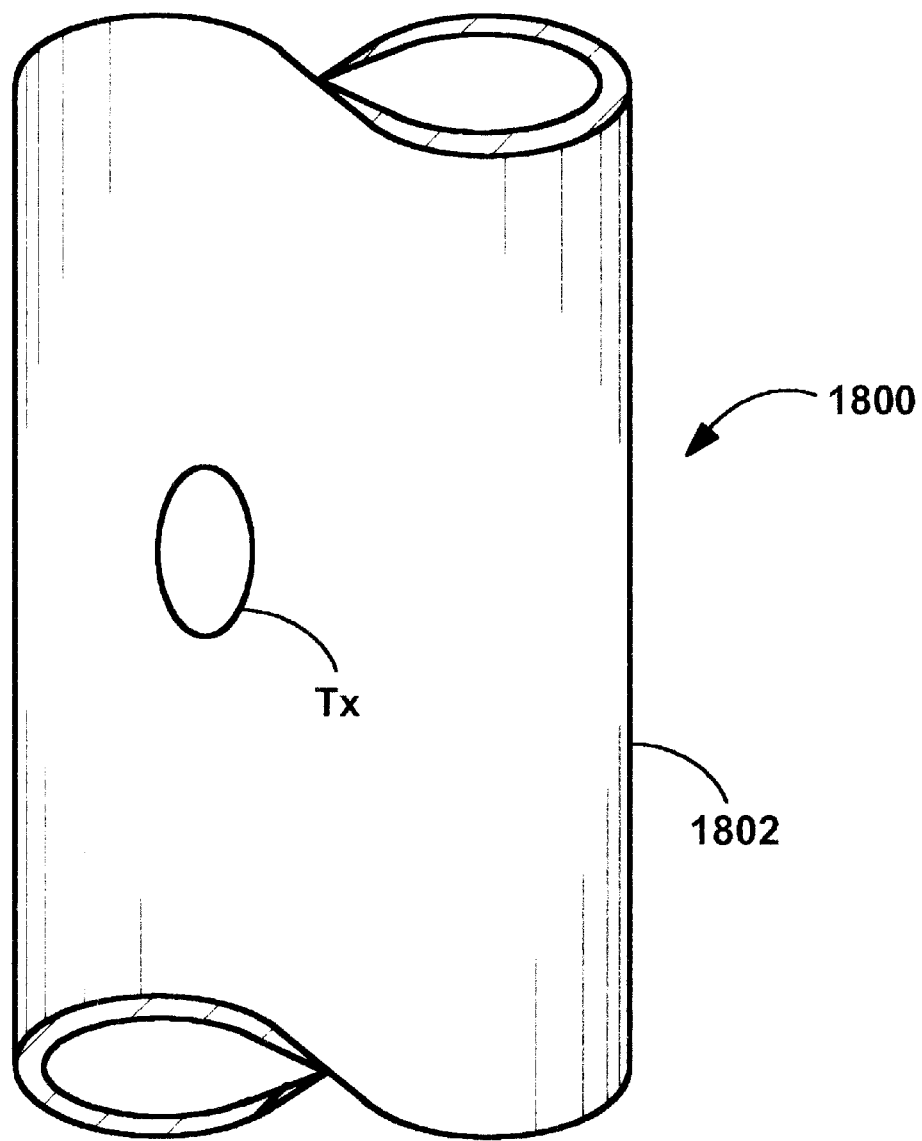
FIG. 18 is a combination transmitter/receiver configuration using the same antenna Tx for practicing the present invention.

FIG. 18 is a combination transmitter/receiver configuration 1800 using the same antenna Tx for practicing the present invention. Signal detection is by the very accurate measurement of voltage and current absorbed in the target material, for example, a substance flowing through a pipe 1802. The combined transmittal/receiver configuration 1800 illustrated in FIG. 18 has a single transmitter/receiver coil. The single coil is transmitted, turned off and used as a receiver for making the accurate measurement of voltage in current absorbed into the target material.

Figure 19A:
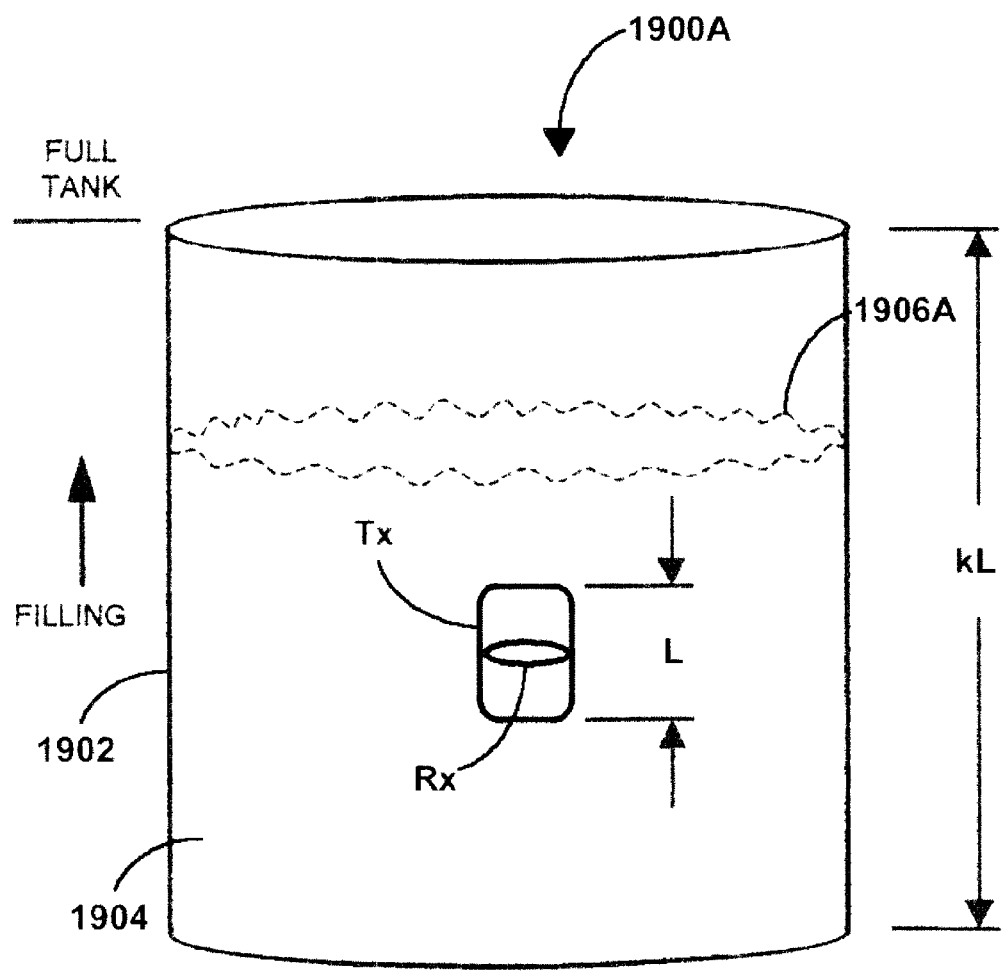
FIG. 19A is an illustration of an application of the present invention utilizing a loop transmitter with a tank for detecting the level within the tank.

FIG. 19A is an illustration of an application of the present invention utilizing a loop transmitter Tx with a tank 1902 for detecting the level 1906A within the tank 1902 or the resistivity. The tank 1902 is illustrated having embedded transmitter/receiver configuration similar to that illustrated in FIG. 14B. The transmitter Tx has a diameter L. The receiver Rx can be moved within the transmitter Tx throughout the distance L. The tank 1902 is provided having a distance of k times that of the movable area for the receiver Rx within the transmitter Tx. Thus, the tank 1902 has depth of kL. The transmitter/receiver configuration can be nulled with water in the tank. As the water starts to fill the tank as the target material, the null signal is offset until such time as the water engages the location of the receiver Rx which would be the maximum offset of the null. As the fluid continues to fill the tank, the null signal would decrease to a lower value.

Figure 19B:
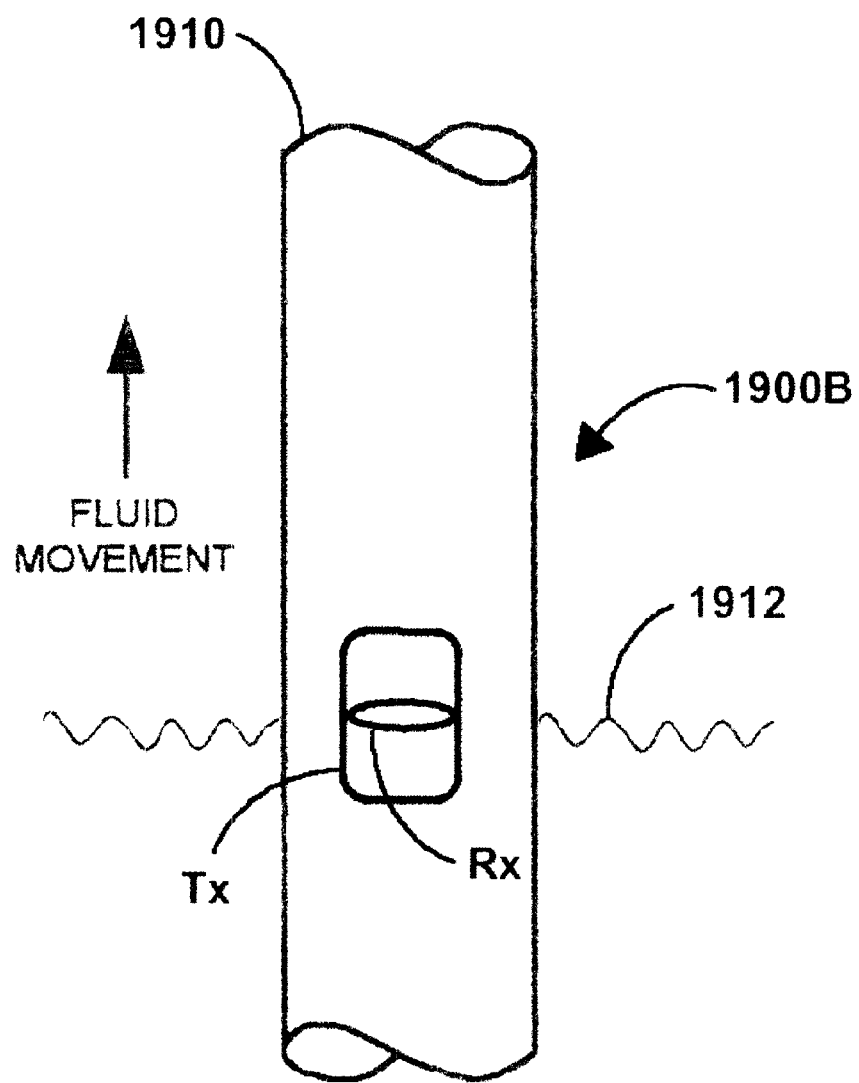
FIG. 19B is an illustration of an application of the present invention utilizing a loop transmitter with a pipe for detecting the level associated with the pipe.

Similarly, FIG. 19B is an illustration of an application of the present invention utilizing a loop transmitter Tx with a pipe 1910 for detecting the level 1912 associated with the pipe 1910. The same measurement can be made within a stainless steel casing having an embedded transmitter/receiver configuration. The transmitter/receiver configuration provides that a receiver Rx is moveably embedded within a transmitter Tx so that nulling can be very accurate.

Figure 20:
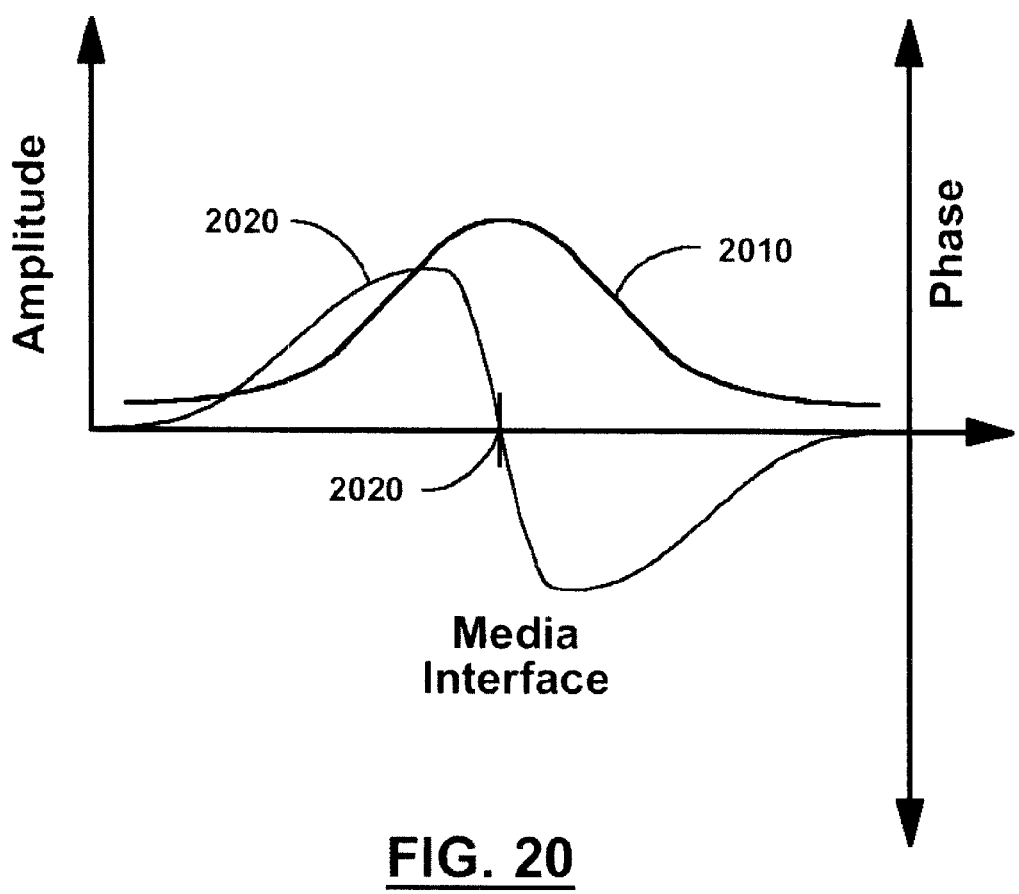
FIG. 20 is a graph of the output of the embedded transmitter/receiver configuration as illustrated in FIGS. 19A and 19B.

FIG. 20 is a graph of the output of the embedded transmitter/receiver configuration as illustrated in FIGS. 19A and 19B. As the fluid begins entering the tank, the volts detected increases 2010. The volts detected will continue to increase until such point as the fluid is located congruent with the receiver Rx, which will be the maximum amplitude 2010. As the fluid continues to fill the tank, nulling offset will decrease and approach the nulled value 2010. The phase of the signal 2020 is disposed over the amplitude 2010 such that the phase increases to a maximum point and as the fluid engages the receiver Rx, the phase 2020 decreases and passes through the zero axis as the fluid rises above the receiver Rx. The phase has a corresponding configuration in the negative as it had in the positive of the graph.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. A method for the measurement of electrical properties of materials through non-magnetizable objects to calculate changes of the material with unknown permeability and conductivity using transparencies comprising the steps of:

(a) creating a first set of electromagnetic waves having specific constant amplitude of a known frequency, the first set of electromagnetic waves for engaging a material of unknown permeability and conductivity, (b) impinging the first set of electromagnetic waves on the material usings transparencies under investigation, (c) receiving a signal, (d) nulling the received signal, (e) creating a change in the material, and (f) receiving a modified signal associated with the change from the nulled signal such that the modified signal contains sufficient information to determine the change in the material.

2. The method of claim 1 for the measurement of electrical properties of materials through non-magnetizable materials to calculate the thickness of a material with unknown permeability and conductivity using transparencies further comprising the steps of:

(a) testing empirically to approximate the conductivity;

(b) testing empirically to approximate the permeability;

(c) creating a second set of electromagnetic waves adjacent to the system to be measured, the second set of electromagnetic waves being of a relatively low frequency and the lower frequency that the first set of electromagnetic waves; and (d) impinging the second set of electromagnetic waves on the system for saturating a portion of the material in the system.

* * * * *